US008639485B2

(12) United States Patent
Connacher et al.

(10) Patent No.: US 8,639,485 B2
(45) Date of Patent: Jan. 28, 2014

(54) SYSTEMS AND METHODS FOR EDITING A MODEL OF A PHYSICAL SYSTEM FOR A SIMULATION

(75) Inventors: Hugh Connacher, Thurmont, MD (US); Robert B. Falk, Takoma Park, MD (US); Milan Ikits, Gaithersburg, MD (US); Michael DiCuccio, Rockville, MD (US); Donald D. Nelson, Montgomery Village, MD (US); Louai Adhami, Gaithersburg, MD (US); Iyanka Ponnamperuma, Rockville, MD (US); Dhananjay Joshi, Germantown, MD (US); Lionel Grenier, Montrouge (FR)

(73) Assignee: Immersion Medical, Inc., Baltimore, MD (US)

( * ) Notice: Subject to any disclaimer, the term of this patent is extended or adjusted under 35 U.S.C. 154(b) by 620 days.

(21) Appl. No.: 11/599,521

(22) Filed: Nov. 14, 2006

(65) Prior Publication Data

US 2007/0124128 A1 May 31, 2007

Related U.S. Application Data

(60) Provisional application No. 60/736,753, filed on Nov. 14, 2005.

(51) Int. Cl.
*G01N 33/48* (2006.01)
*G01N 31/00* (2006.01)
*G06G 7/48* (2006.01)
*G06G 7/58* (2006.01)

(52) U.S. Cl.
USPC ............... 703/11; 703/12; 702/19; 702/22

(58) Field of Classification Search
None
See application file for complete search history.

(56) References Cited

U.S. PATENT DOCUMENTS

| 5,731,804 | A | 3/1998 | Rosenberg |
| 5,956,040 | A | 9/1999 | Asano et al. |
| 6,074,213 | A | 6/2000 | Hon |
| 6,381,562 | B2 * | 4/2002 | Keane ............................ 703/11 |
| 7,460,104 | B2 * | 12/2008 | Rosenberg ................... 345/156 |
| 2003/0112269 | A1 | 6/2003 | Lentz et al. |

(Continued)

FOREIGN PATENT DOCUMENTS

| JP | 10-323335 | 12/1998 |
| JP | 11-053347 | 2/1999 |

(Continued)

OTHER PUBLICATIONS

Patent Cooperation Treaty, International Search Report, International Application No. PCT/US2006/044266, mailed Jun. 28, 2007, 5 pages.

(Continued)

*Primary Examiner* — Larry D Riggs, II
(74) *Attorney, Agent, or Firm* — Kilpatrick Townsend & Stockton LLP

(57) ABSTRACT

Systems and methods for modifying a medical model of a physical system is disclosed. One disclosed system includes a graphical user interface configured to display at least one parameter associated with the medical model and receive a modification of the at least one parameter. The system also includes a processor configured to receive the modification of the at least one parameter from the graphical user interface and execute a simulation of a part of the medical model including the modification of the at least one parameter.

27 Claims, 22 Drawing Sheets

(56) References Cited

U.S. PATENT DOCUMENTS

| | | | |
|---|---|---|---|
| 2004/0193393 A1* | 9/2004 | Keane | 703/16 |
| 2005/0093847 A1 | 5/2005 | Altkorn et al. | |
| 2005/0162383 A1 | 7/2005 | Rosenberg | |
| 2005/0187747 A1 | 8/2005 | Paxson et al. | |

FOREIGN PATENT DOCUMENTS

| | | |
|---|---|---|
| JP | 11-085820 | 3/1999 |
| JP | 11-197159 | 7/1999 |
| WO | WO 03/079149 A2 | 9/2003 |

OTHER PUBLICATIONS

State Intellectual Property Office of the People's Republic of China, Notification of the First Office Action, Application No. 200680042465.7, issued Jul. 31, 2009.

State Intellectual Property Office of the People's Republic of China, Notification of the Second Office Action, Application No. 200680042465.7, issued Jul. 12, 2010.

Japanese Patent Office, Notification of Reasons for Rejection, Application No. JP 2008-540285, dated Feb. 9, 2012.

State Intellectual Property Office of the People's Republic of China, Third Office Action, Application No. 200680042465, dated Jan. 12, 2011.

* cited by examiner

SYSTEMS AND METHODS FOR EDITING A MODEL OF A PHYSICAL SYSTEM FOR A SIMULATION

CROSS-REFERENCES TO RELATED APPLICATION

This patent application claims priority to U.S. Provisional Patent Application No. 60/736,753 entitled "Editor for an Endovascular Simulation Training Device" filed Nov. 14, 2005, the entirety of which is hereby incorporated by reference.

FIELD OF THE INVENTION

The present invention generally relates to editors for computer software, and more particularly relates to editors for computer simulations.

BACKGROUND

Simulators of physical systems have been used in the past for providing a training environment for physical systems that may be too costly or dangerous to learn by performing the actual activity. For example, a flight simulator may be used to teach a pilot skills used in flying an airplane without subjecting the pilot to the risk of damaging an actual airplane or injuring the pilot. However, editing a model of an airplane or a portion of an airplane for use in a simulator conventionally requires editing the model and testing the modified model within the full simulator, rather than testing only the modified component without having to run a full simulation. Further, conventional computer simulators do not allow the modification and testing of discrete elements of the model being simulated.

SUMMARY

One illustrative embodiment of the present invention comprises a system for modifying a model of a physical system, comprising a graphical user interface configured to display at least one parameter associated with the model of the physical system, and receive a modification of the at least one parameter. The illustrative embodiment further comprises a processor configured to receive the modification of the at least one parameter from the graphical user interface, and execute a simulation of a part of the model of the physical system including the modification of the at least one parameter. An input device may be in communication with the processor, the input device may be configured to transmit an input signal to the processor, the input signal associated with a state of the input device. The illustrative embodiment may further comprise an actuator configured to receive an actuator signal and apply a force to the input device, the force based at least in part on the input signal and the simulation of the part of the model of the physical system using the modification of the at least one parameter.

Another embodiment of the present invention comprises a method for editing a model of a physical system comprising displaying at least one parameter associated with the model of the physical system, receiving a modification of the at least one parameter, and executing a simulation of a part of the model of the physical system including the modification of the at least one parameter. In another embodiment, a computer-readable medium comprises code for a carrying out such a method.

These illustrative embodiments are mentioned not to limit or define the invention, but to provide examples to aid understanding thereof. Illustrative embodiments are discussed in the Detailed Description, and further description of the invention is provided there. Advantages offered by various embodiments of this invention may be further understood by examining this specification.

DETAILED DESCRIPTION

Figure 1:
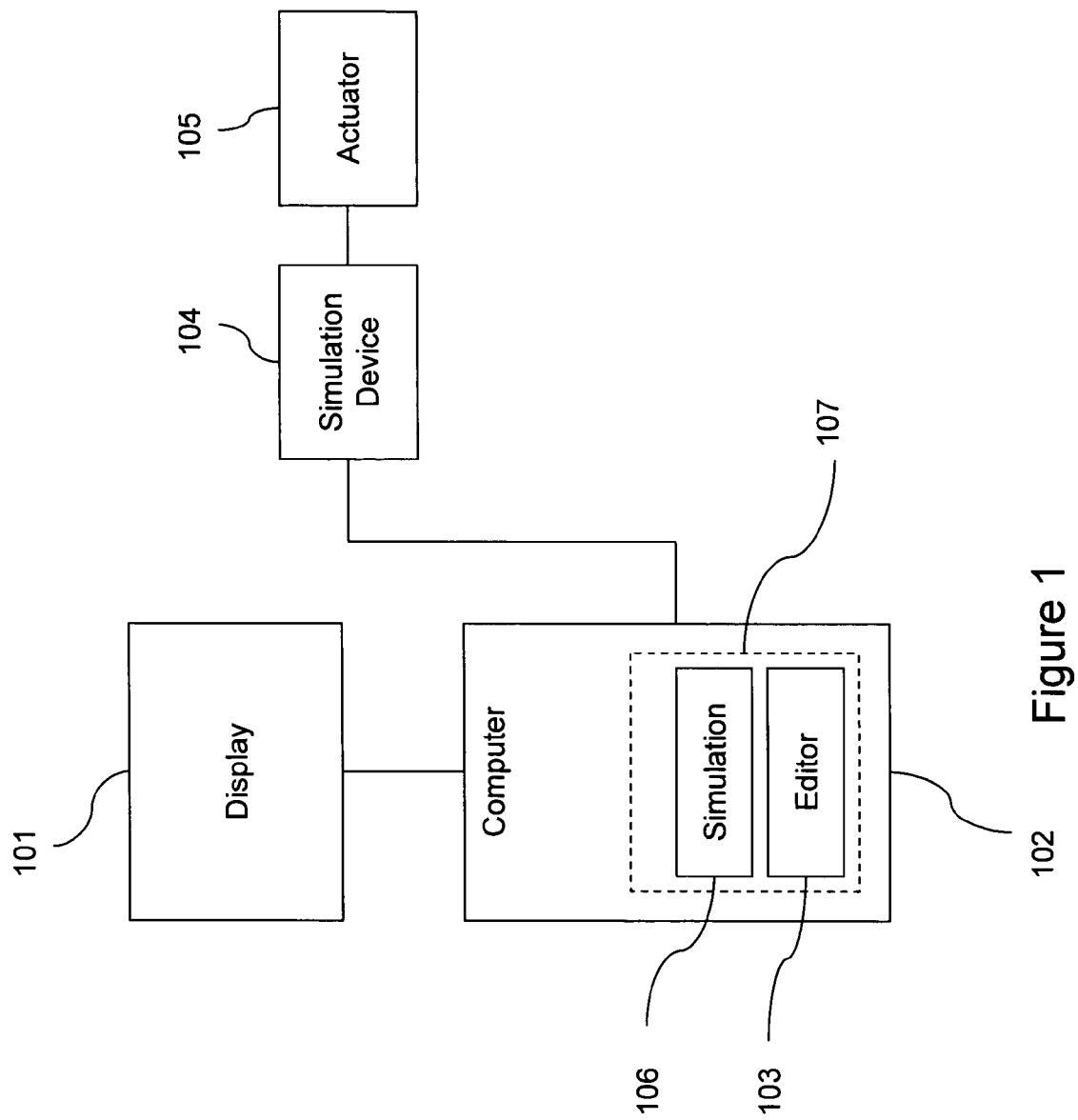
FIG. 1 shows a block diagram of one embodiment of the present invention of a system for editing a model of a physical system for a simulation.

Embodiments of the present invention provide systems and methods for editing a model of a physical system for a simulation.

Illustrative Endovascular Simulation Editor

In one embodiment of the present invention, a user employs an editor to edit one or more characteristics of an endovascular system for use by a simulation program. After a user modifies one or more of the characteristics, the user is able to execute a simulation of the modified portion of the model without executing a full simulation employing the entire model within a simulated environment. For example, a user may modify a thickness characteristic associated with a wall of a chamber of a human heart. The user may then execute of a simulation of just the modified wall, for example to display or interact via an input device, to isolate and test the modified portion of the heart. This may provide a user with a faster, more focused test of a modified characteristic than may be practical within a simulation of the entire model within a simulation context.

This illustrative example is given to introduce the reader to the general subject matter discussed herein. The invention is not limited to this example. The following sections describe various embodiments of systems and methods for editing a model of a physical system for a simulation.

Illustrative Systems of a Simulation Program

In one embodiment of the present invention, a model of a physical system includes a construct that describes various characteristics of the physical system. For example, a model of a human heart may include a data file that contains characteristics of the heart, including the size and shape of the heart, the size and shape of the heart's chambers, the thickness of the walls of the heart at various locations, or other characteristics. The characteristics in the construct of a model may comprise many different aspects of the modeled physical system, including structural, electrical, vibrational, and other characteristics. For example, a model of a heart may comprise structural characteristics, as well as information relating to blood vessels, nerves, tissue, and other biological systems associated with the heart.

Such a model may be employed within a simulation program to allow a user of the simulation program to interact with the model in order to train the user in the use or manipulation of the physical system. For example, a simulation program employing a model of the human heart may allow a medical student to study the heart or to perform simulated surgical procedures on the modeled heart without having to perform an actual heart surgery.

Such models may also be used in simulations of minimally invasive surgery (MIS). MIS is a field of surgery that crosses all medical disciplines. In MIS, operations are performed using specialized instruments designed to fit into the body through tiny punctures instead of through one or more large incisions. MIS technology is credited in large part with the fact that nearly half of all surgery today is ambulatory, or performed on an outpatient basis. MIS usually results in less pain, scarring and recovery time for the patient, as well as reduced health-care costs (due to shorter hospitalization).

Over the last decade or more, percutaneous (access to blood vessels made through the skin) coronary interventions (PCI) have been replacing open heart surgeries. Balloons and stents (small wire mesh tubes) have been incorporated into PCI in the treatment of atherosclerosis, and are known as Percutaneous Transluminal Coronary Angioplasty (PTCA), where transluminal refers to procedures performed within the blood vessel. Catheters, which are thin flexible tubes, are used with guide wires to gain access to different parts of the patient's anatomy. Balloons and stents are then used to open up blockages providing for a reperfusion of the target organ or body system. Balloons and stents can be placed in the heart, brain, kidneys, abdomen, legs and neck.

To provide a variety of training scenarios, it may be advantageous to provide a plurality of differing models of a physical system. For example, hearts of different sizes, shapes, ages, and with different pathologies may be modeled to provide a breadth of training simulations for a medical student. To provide different variations of the model of the human heart, it may be advantageous to create a basic model of the human heart that may be later modified or customized, rather than start over with a new model for each desired variant.

In one embodiment of the present invention, an editor of a model of a physical system for a simulation comprises a computer system executing computer software. The computer software comprises a graphical user interface. The graphical user interface may allow a user to view and manipulate a graphical representation of the model of a physical system, such as a medical model of a human heart. While a human heart is used as an example of a physical system that may be modeled, medical models of physical systems may include other organs or portions of the human body, organs or portions of other plants or animals, or other biological organisms, such as bacteria, viruses, and embryos. Other physical systems may be modeled in addition to medical models, such as models of mechanical or electrical systems, or subsystems or potions of mechanical, electrical, or other types of physical systems. In one embodiment, a user of the editor may be able to rotate, zoom, select a portion of the model, select a particular layer or subsystem of the model, or perform similar operations that allow the user to accurately edit a desired attribute or parameter associated with the model. In addition, it may be advantageous for the user to be able to isolate and test a modification without running a full simulation of the model in a simulated environment. Further, it may be advantageous to allow a user to interact with the model, or the portion of the model, that is modified to more closely examine the modification made to the model.

The user may also be able to modify one or more characteristics or parameters of the model using the illustrative embodiment. For example, a user may be able to modify a structural characteristic of a model, such as size or shape. A user may be able to modify subsystems or subsections of a model, such as electrical subsystems, hydraulic subsystems, muscular subsystems, or other subsystems or subsections within the model.

For example, a model may represent a human heart. One embodiment of the present invention may allow a user to adjust the size of the heart, the thickness of a wall of the heart, the placement or shape of one or more chambers within the heart, or the shape of the heart using one or more of the interface elements, such as a menu, window, slider bar, dial, or other implement. For example, a user may be able to open a window relating to the shape of the heart wherein the window comprises one or more parameters and corresponding values. A user may be able to change the value of one or more of the parameters, which may then cause a corresponding change in the model of the human heart. A change in a parameter may also alter the graphical representation of the model, providing visual feedback to the user of the modification. Further, a modification may cause a change in a feel, or haptic effect, associated with the model. For example, a modification to a thickness of a wall of a heart may cause an increased in resistance to an input device or surgical tool interacting with the modified wall. In one embodiment, a change in an electrical characteristic of a heart may cause an increased vibration on an input device corresponding to an increased strength of contraction of the heart. A variety of other haptic effects may also be provided, such as resistive haptic effects, active haptic effects, and vibrotactile effects.

One illustrative system for editing a model of a physical system also comprises an input device in communication with the computer or other processor-based device. An input device may be any device used to interact with a computer. For example, an input device may be a keyboard, a mouse, a joystick, or a touch screen. An input device may also be a simulation device that is used to interact with a simulation. For example, a simulation device may be a tool used with a simulation relating to the model being edited, and may be used to test modifications made to the model. For example, a simulation device may be a medical tool, such as a catheter, associated with a simulated procedure involving a human heart may be used to test a change in the size of a blood vessel that supplies nutrients to the heart. In other embodiments of the present invention, a simulation device may be a medical device such as a laparoscope, a syringe, an intravenous needle, a scalpel, or other tool that may be used in surgery or other medical procedures. In some embodiments, a simulation device may also be a device or implement appropriate for another type of simulation, such as a joystick, steering wheel, yoke, throttle, or similar implement.

In one illustrative embodiment, the input device may be haptically-enabled. In such an embodiment, an actuator may be coupled to the input device to provide haptic effects to the input device, which may provide a more realistic simulated interaction with the model. For example, a user may test a modification to a model of the heart by simulating the insertion of a catheter into a blood vessel, whose diameter has been modified. During testing, the processor may transmit a signal to the actuator to cause a force to be output on the input device. For example, if the diameter of the blood vessel to be tested has been reduced within the editor, the processor may transmit a signal to the actuator to cause the actuator to apply a resistive force to the simulation tool to simulate movement of a catheter through a smaller blood vessel.

Thus, this illustrative embodiment provides a system for editing a model of a physical system within a graphical user interface executed by a computer or other processor-based device. The system may allow a user to interact with the graphical user interface to rotate or zoom into or out of a graphical representation of the model. The system may further allow a user to modify the model one or more parameters that define the model through menus, windows, or other interface elements. The system may further allow a user to test a modification to the model by using a haptically-enabled input device to interact with the modified portion of the model, or with the entire model. Thus, the illustrative system may enhance the ease and speed of development of different simulation scenarios that may be created from a basic model of a physical system. It may further provide a more accurate model as the model may be more easily tuned to provide a particular haptic response or feel.

Illustrative System

Referring now to the figures in which like numerals refer to like elements throughout the several figures, FIG. 1 shows a block diagram of one embodiment of a system 100 for editing a model of a physical system for a simulation. The embodiment shown in FIG. 1 comprises a display 101 coupled to a computer 102. An input device 104, which may also be referred to herein as a surgical instrument, is in communication with computer 102 and actuator 105. The computer 102 is configured to execute an editor 103, which comprises a graphical user interface capable of being displayed on display 101. The computer is also configured to execute a simulation 106 of the model.

In one embodiment, computer 102 may comprise a processor or processors (not shown). The processor comprises a computer-readable medium 107, such as a random access memory (RAM) coupled to the processor. The processor executes computer-executable program instructions stored in memory, such as executing one or more computer programs for editing a model of a physical system. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example computer-readable media, that may store instructions that, when executed by the processor, can cause the processor to perform the steps described herein as carried out, or assisted, by a processor. Embodiments of computer-readable media may comprise, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

In the embodiment shown in FIG. 1, the computer 102 is configured to store, load, import, and otherwise save and load data from a non-volatile memory device, such as a hard drive.

In one embodiment, the computer 102 may comprise a memory, for example a hard drive, configured to store program code for implementing the editor 103. The computer 102 may be in communication with a display 101. In one embodiment, computer 102 may execute editor 103 and cause a graphical user interface (GUI) to be shown on display 101. A user may interact with the graphical user interface, for example, with a keyboard, mouse or other input device. For example, a user may be able to load a model of a physical system from a memory device, modify the model, and store the modified model to the memory device. The user may further be able to cause the computer 102 to execute a simulation of the model, or a portion of the model, including the modifications made to the model.

If a user causes the computer 102 to execute the simulation 106, the computer may receive signals from the input device 104. These signals may be referred to herein as input signals. The computer 102 may further transmit signals to the input device 104 and/or to the actuator 105. Signals sent from the computer 102 to the input device 104 may be referred to herein as output signals. Signals sent from the computer 102 to the actuator 105 may be referred to herein as actuator signals. For example, the computer may transmit a signal to the actuator 105 to cause a force to be output on the input device 104. Such a force may be configured to cause a haptic effect and may be resistive, active, vibrational, or another type of force, as will be more fully explained below.

Display 101 may comprise one of many different varieties of display devices. For example, display 101 may comprise a cathode-ray tube (CRT) monitor, a liquid crystal display (LCD), or other display device capable of receiving signals from the computer 102 and generating a visible representation of the signals. In one embodiment, display 101 may comprise a touchscreen or other touch-sensitive display screen.

Simulation device 104 may comprise a device capable of transmitting a signal to the computer 102, indicating a state of the input device 104. For example, in one embodiment, input device 104 may transmit a signal to computer 102 indicating a position of the input device 104. In one embodiment, input device 104 may transmit a signal to computer 102 indicating a velocity of the input device 104. In one embodiment, input device 14 may transmit a signal to computer 102 indicating an orientation, a rotation, a translation, an acceleration or other information related to a state of the input device 104.

In some embodiments, input device 104 may comprise a device configured to simulate a medical procedure. For example, input device 104 may comprise a device configured to simulate the insertion of a catheter into a blood vessel. In one embodiment, input device 104 may comprise a device configured simulate a syringe. In one embodiment, input device 104 may comprise a laparoscopic input device. Other devices suitable for simulating medical procedures may be used as well, such as the devices described in U.S. Pat. No. 5,731,804 entitled "Method and Apparatus for Providing High Bandwidth, Low Noise Mechanical I/O for Computer Systems," the entirety of which is hereby incorporated by reference.

In an embodiment, the input device 104 may also include, but is not limited to, a mannequin, angiographic/guiding catheters, diagnostic/therapeutic wires, balloon/stent catheters, manifold/injection of contrast and medications, a balloon inflation device, fluoroscopy equipment, a C-arm control, a dual screen interface, a foot pedal for cine and fluoro controls, and/or an embolic protection device and a basket to catch free flowing debris. The input device 104 may be configured to track user motions to simulate the insertion of a variety of interventional devices such as a stent, pace maker lead, or catheter and balloon occlusive distal protection device used to block downstream flow of debris.

In some embodiments, an input device 104 may comprise a device configured to simulate the control of a vehicle or of a video game. For example, in one embodiment, input device 104 may comprise a steering wheel, a joystick, a joypad, a gamepad, a button, a switch, a trackball, or other suitable device.

In one embodiment, the input device 104 may be capable of providing a haptic response to a user. The haptic response may provide the user with a tactile (touch) sensation based on sensed position, velocity, orientation, or other state of the input device 104. While using the input device 104 as an input/output device, the user may receive feedback from the computer 102 in the form of sensations felt by the user's hand or other parts of the user's body. In combination with a visual display 101, the editor 103 may allow a user to modify parameters associated with a model, and then interact with the modified portion of the model using the haptically-enabled input device 104 to determine how the modifications affect the "feel" of the model.

In some embodiments, input device 104 may be in communication with an actuator 105. In one embodiment, actuator may be configured to receive an actuator signal from the computer 102 and output a force to input device 104. In one embodiment, actuator 105 may be configured to provide resistive haptic effects to input device 104. For example, actuator 105 may be configured to resist the movement of the input device 104 in one or more degrees of freedom. In one embodiment, actuator 105 may be configured to provide active haptic feedback. For example, actuator 105 may be configured to provide vibrational effects to the input device 104. For example, in one embodiment, actuator 105 may be configured to provide vibrational effects to input device, wherein the vibrational effects are configured to impart a feeling of a heartbeat or of fluid flowing across or past the input device 104.

In one embodiment, actuator 105 may comprise a plurality of actuators. For example, in one embodiment, actuator 105 may comprise two actuators; a first actuator configured to provide active haptic feedback, and a second actuator configured to provide resistive haptic feedback. In some embodiments, multiple actuators to provide either active haptic effects or resistive haptic effects may be used in a variety of combinations. For example, in one embodiment, input device 104 may be movable in three degrees of freedom. In such an embodiment, actuator 105 may comprise six actuators. A pair of actuators may be employed for each of the three degrees of freedom, wherein each pair of actuators may comprise an actuator configured to provide resistive haptic effects, and an actuator configured to provide active haptic effects. In one embodiment, actuator 105 may be configured to provide both resistive and active haptic effects. In one further embodiment, an actuator may be configured to provide a vibrotactile response.

Actuator 105 may comprise one or more of many different types of actuator. For example, in one embodiment, actuator 105 may comprise a piezo-electric actuator. In one embodiment, actuator 105 may comprise an electromagnetic actuator. Other embodiments may comprise motors, brakes, solenoids, eccentric-rotating masses, and/or multi-function actuators. For example, in one embodiment, an input device comprising a catheter may comprise an electromagnetic actuator configured to provide a braking force on the input device. When the actuator is energized, the actuator may cause a brake surface to contact the input device, which may thereby cause a resistance to the movement of the input device. In another embodiment, an linear resonant actuator may be used to provide a vibrational effect, such as, for example, to simulate blood flow or a heartbeat Still other types of actuators may be used in one or more embodiments of the present invention.

In one embodiment, the system 100 may be configured to create a model of a physical system that may be editable using the editor 103, such as, for example, a model of an internal organ of a patient to be operated on (referred to herein as the "virtual organ"). In one embodiment, the system 100 may be able to evaluate magnetic resonance imaging (MRI) data of a patient's heart to create a three dimensional representation of the chambers of the heart. The three dimensional representation of the paths of the cardiac venous anatomy may be constructed in the system as well. The surgeon can utilize the system in evaluating the data, and constructing a reasonable approximation of the patient's heart for use in the simulation of the system. The system 100 may therefore be able to import data taken from tests of the patient's anatomy and provide the geometry of the patient's organ on the display. The system thus may provide the surgeon with a virtual replica of the patient's organ such that the surgeon is able to practice a surgery beforehand and examine different methods for overcoming any difficulties that may be present in the specific case. It should be noted that although the model discussed herein is a heart, embodiments of the present invention may allow editing of a model of any physical system, including biological systems, mechanical systems, electrical systems, or other systems.

In one embodiment, the system is capable of modifying the patient's virtual organ to simulate a mishap or other complication that could occur during surgery. For example, an existing virtual organ can be modified in the editor in the system, whereby the geometry around the coronary sinus is modified to make insertion of the cannula more challenging to the surgeon. In another example, the structure and geometry of the cardiac veins may be manipulated to make accessing the most likely target vessel more difficult. In yet another example, the areas of the organ that can cause complications may be evaluated and changed in the system to make the surgeon reassess his cognitive decision making skills and, as a result, change the target location for the pacing lead. All of these challenges may occur in real cases, which may make the training process more effective.

Illustrative User Interfaces

Figure 2:
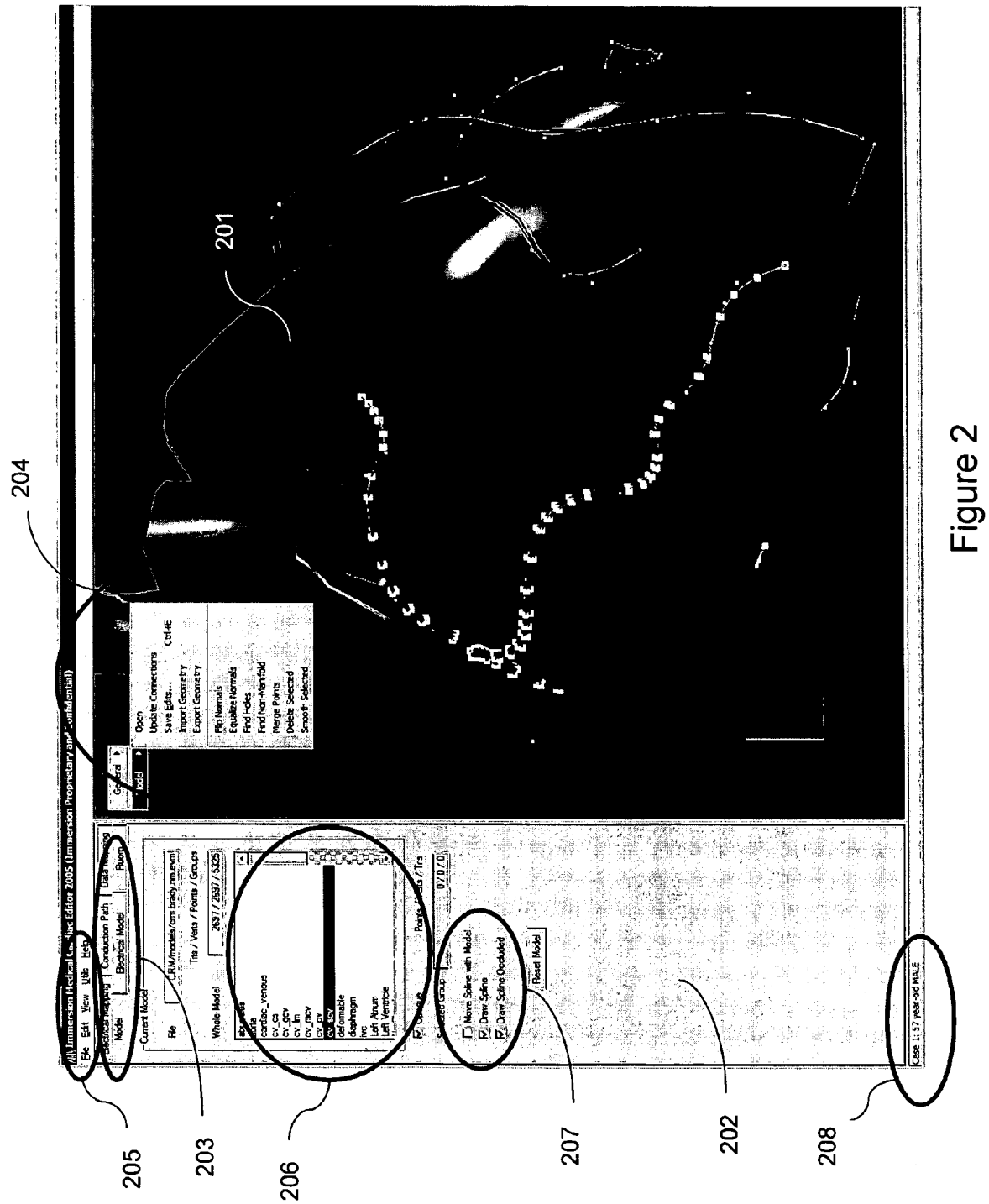
FIG. 2 shows a graphical user interface (GUI) within an editor of a model of a physical system in one embodiment of the present invention.

FIG. 2 shows a graphical user interface (GUI) 200 within an editor 103 of a model of a physical system in one embodiment of the present invention. In the embodiment shown, the GUI comprises a graphical representation of a model 201 of a physical system, a human heart. The GUI shown in FIG. 2 also comprises a window 202 which comprises a plurality of tabs as well as a list of items associated with the model of a human heart 201, different graphical representations and views of which are shown throughout the figures. A user may interact with the GUI shown in FIG. 2 by selecting one or more items from the list, selecting one or more tabs, by interacting with a context-sensitive menu 204, or by selecting an option from a drop-down menu 205. Some embodiments may comprise additional interface elements or may comprise additional ways to interact with the GUI. For example, in one embodiment, the GUI may allow a user to directly interact with the graphical representation of the model, such as by rotating the model by selecting with a cursor, and moving the cursor. Other GUI elements that may be advantageous in some embodiments of the present invention would be known to those of ordinary skill in the art.

As shown in FIG. 2, the Model tab, one of a plurality of tabs 203, is shown to be active. The Model tab may allow for the creation and/or modification of the basic geometry of a model, for example, a cardiac geometry. In the embodiment shown, operations performed within this tab may allow a user to either create a new virtual organ or modify an existing virtual organ. Functionality of the Model tab may include, but is not limited to: importing basic geometry (such as, for example, chamber and vascular anatomy) or for exporting geometry, saving/creating geometry in a proprietary format (i.e., an ".evm" file), fixing basic geometric problems (non-manifold edges, holes, incorrect normals, smoothing), moving and/or rotating model points alone, moving and/or rotating model points and spline control points together, and displaying of pertinent model information.

Figure 4:
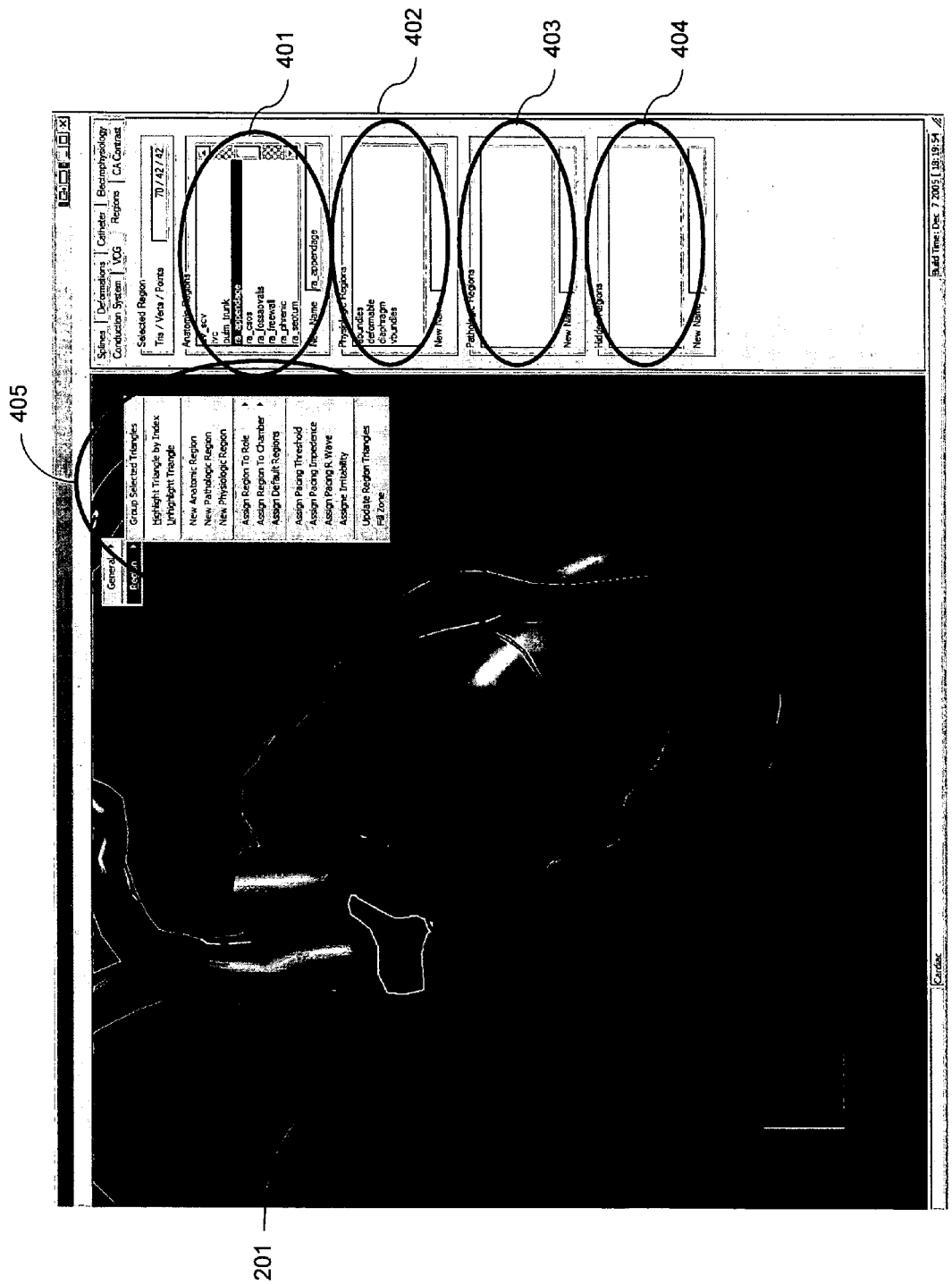
FIG. 4 shows a GUI component for editing a model of a physical system according to one embodiment of the present invention.
Figure 6:
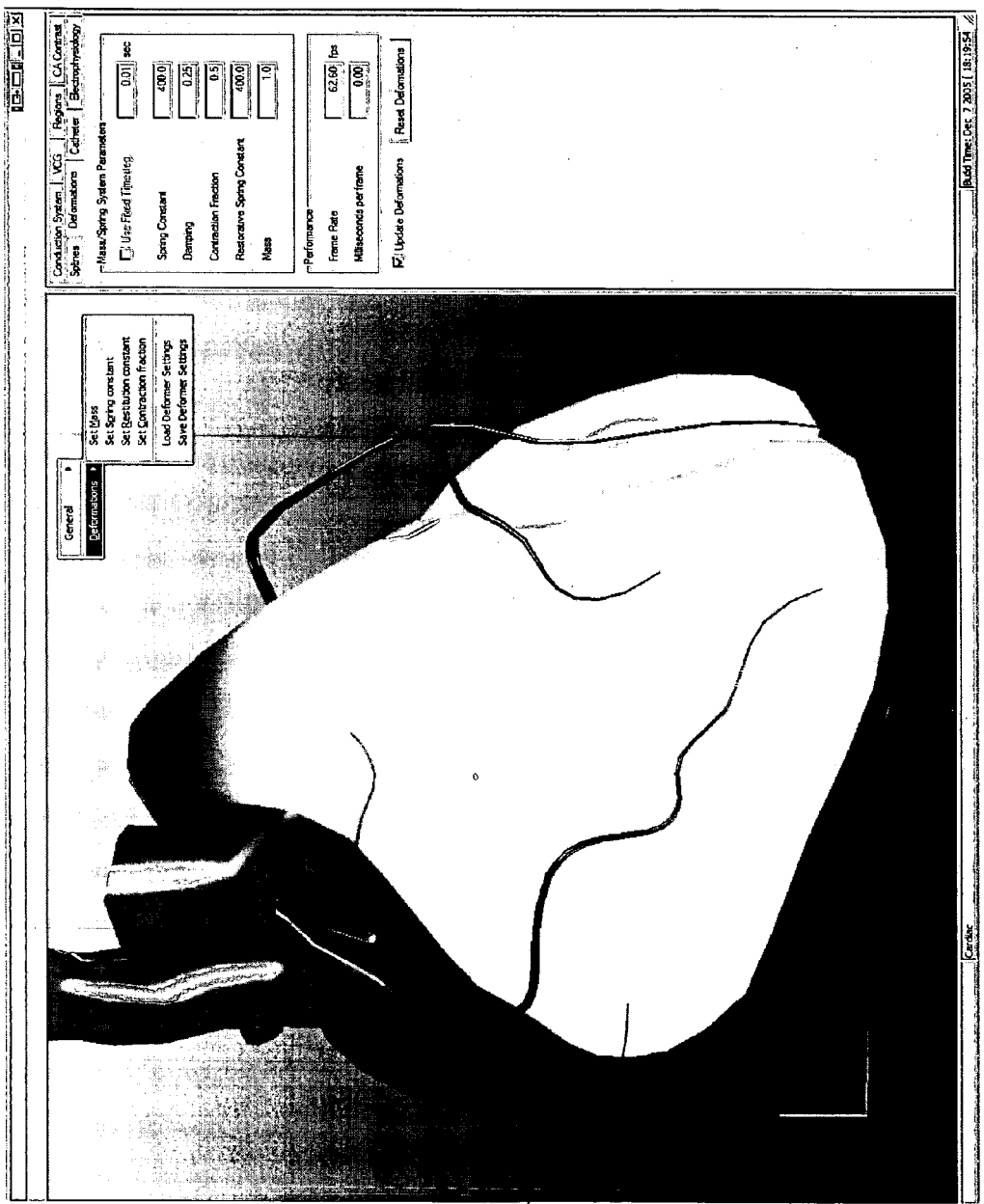
FIG. 6 shows a GUI component for editing a model of a physical system according to one embodiment of the present invention.

Other tabs shown in FIG. 2 include an Electrical Model tab, a Fluoro tab, an Electrical Mapping Tab, a Conduction Path tab, and a Data Mapping tab. These tabs may allow editing of other aspects of a model. Still further embodiments of the present invention may comprise additional tabs, different tabs, or fewer tabs. For example, FIG. 6 shows a Deformations tab according to one embodiment of the present invention. Such a tab may allow editing of parameters related to the movement of the model or of portions of the model. In another example, the embodiment shown in FIG. 4 shows a graphical representation of a human heart. Such an embodiment may allow a user to modify parameters that drive heart motion, such as the location, magnitude, and numerical stability of cardiac contractions.

Figure 3:
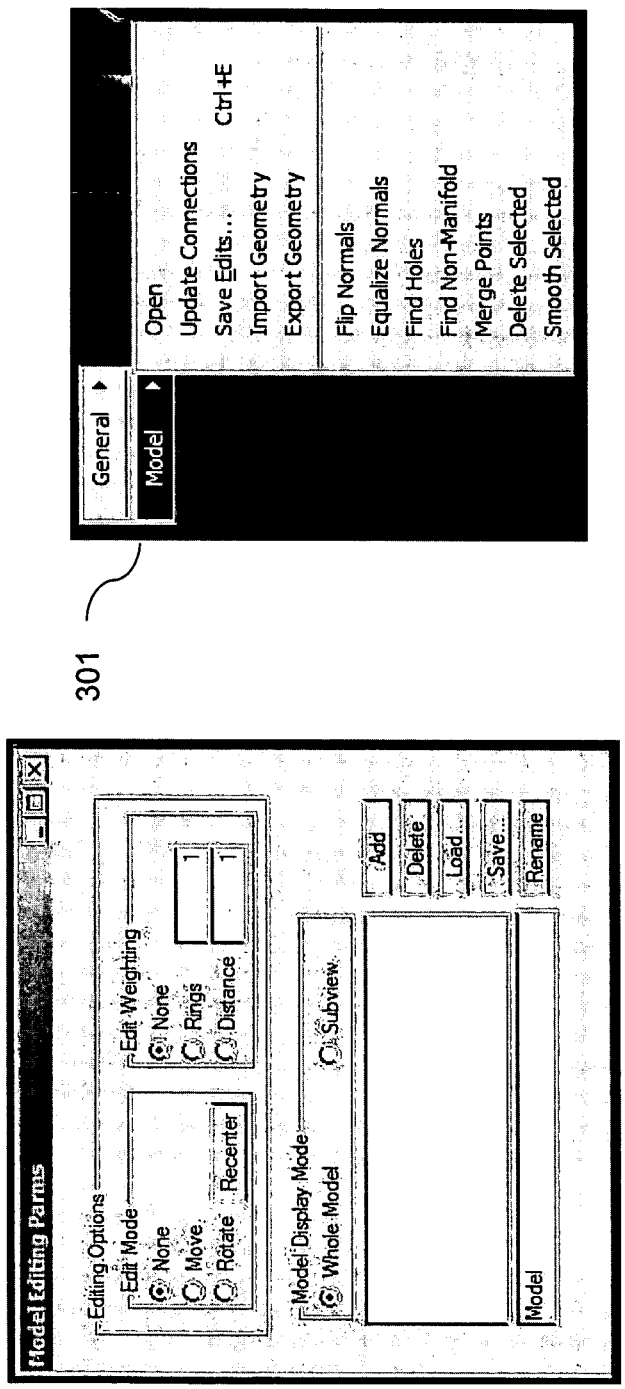
FIG. 3 shows a dialog box and a context-sensitive menu which may allow a user to select an editing mode for a model in one embodiment of the present invention.

A user may interact with the GUI 200 through one or more interface elements. For example, FIG. 3 shows a dialog box 300 and a context-sensitive menu 301 which may allow a user to select an editing mode for a model. For example, a user may select the "Rotate" radio button, which may allow a user to rotate part or the entire model 201. The user may then be able to select a portion of the model 201 and manipulate the portion. For example, model 201 shown in FIG. 2 comprises a polygonal frame. A user may be able to select one point within the polygonal model to move, delete, or otherwise manipulate, thereby changing the shape of the model. A user may further add a point within the polygonal model to change the shape of the model, or modify information or parameters associated with the point.

FIG. 4 shows a GUI component 400 for editing a model of a physical system according to one embodiment of the present invention. The embodiment shown in FIG. 4 allows a user to create, rename, and select regions of a model 201 of a physical system. In the embodiment shown, the model 201 is of a heart, however, other models may be manipulated according to various embodiments of the present invention. As shown in FIG. 4, a user may create, rename, or select anatomical 401, physiological 402, pathological 403, and/or hidden regions 404 of the heart. In one embodiment, a user may be able to move, delete, resize, or otherwise modify one or more regions of the model. A user may select a region to create or modify by interacting with a menu 405. For example, in the embodiment shown, a user may be able to create a new region, assign an existing region to a role (such as anatomic, physiologic, pathologic, or other role), or assign a region to a chamber of the heart. Other modifications may be available in other embodiments. For example, in one embodiment, a user may be able to delete a region from the model. In one embodiment, the GUI component 400 may have options or modifications relating to another portion of a patient's anatomy, such as another internal organ or system (for example the circulatory system), or to a model of another type of physical system, such as a vehicle, an environment or character within a video game, or other type of model.

In one embodiment, a user may be able to view and/or modify only a portion of the model. Such a feature may provide for enhanced ease of editing the model. For example, if a user wishes to edit only a particular chamber of a heart, an editor according to one embodiment of the present invention may allow a user to select a subsection of the model and display the selected subsection. The user may then be able to modify only the selected subsection. In a similar embodiment, a user may be able to customize the subsection to be viewed and/or edited. For example, a user may be able to select points on the model which may define the boundaries of the subsection of the model to be viewed and/or edited.

Figure 5:
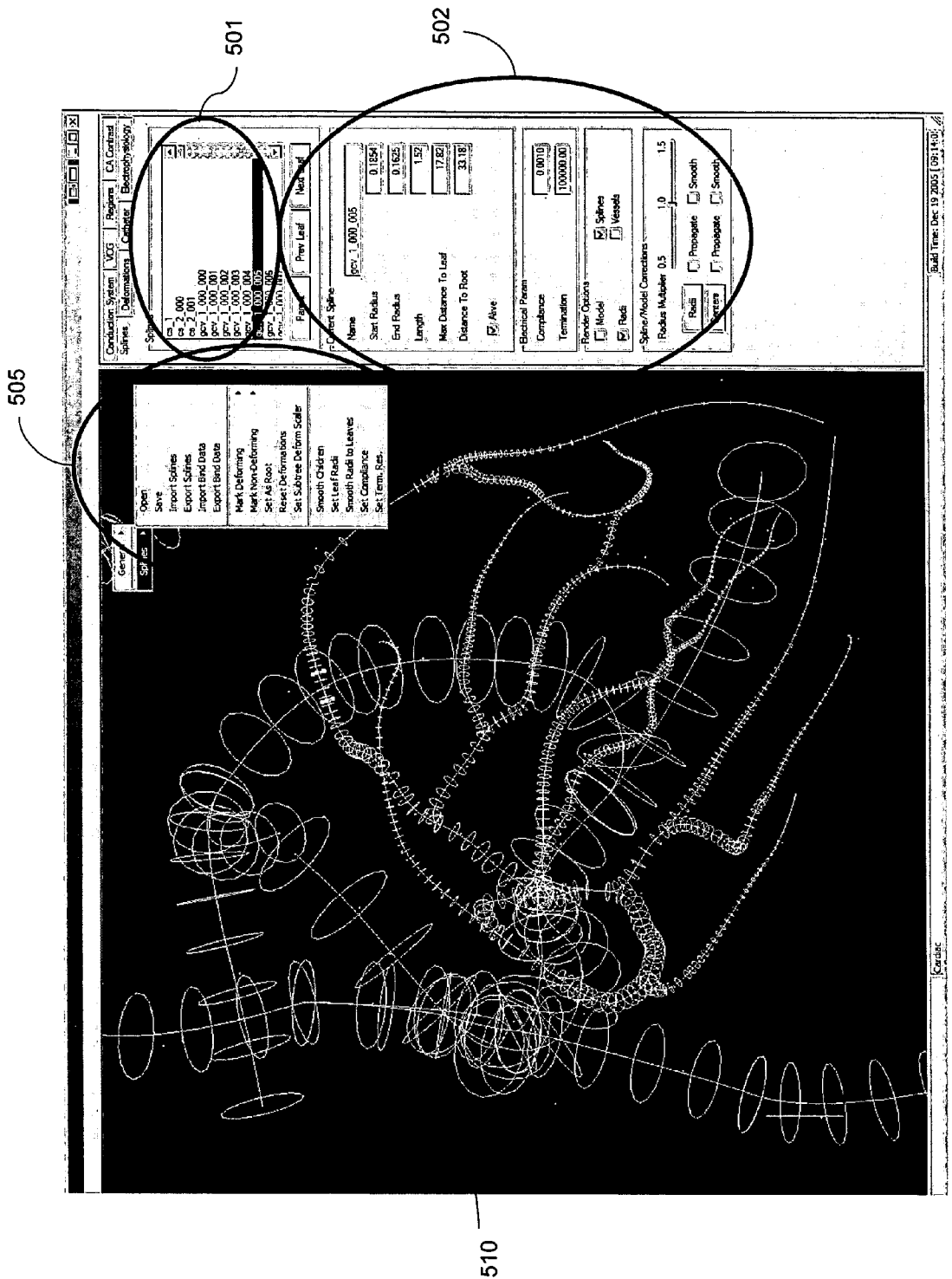
FIG. 5 shows a GUI component for editing a model of a physical system according to one embodiment of the present invention.

FIG. 5 shows a GUI component 500 for editing a model of a physical system according to one embodiment of the present invention. The graphical representation of model 201 in FIG. 5 comprises a graphical representation of splines defining a portion of the structure of the model of the physical system. For example, in the model of the heart 201 shown in FIG. 5, the splines represent the shape of one or more blood vessels 510 associated with the heart 201. In other embodiments, a spline may represent features of a model of a physical system. For example, in one embodiment one or more splines may define a fuel line, a cylinder within an engine block, or other features of a vehicle or engine. In a further embodiment, one or more splines may define a shape and/or texture of a terrain in a video game environment.

According to the embodiment shown in FIG. 5, a user may modify a spline using interface elements provided by the GUI component 500. For example, a user may change the radius of a blood vessel represented by one or more splines, or otherwise change the geometry of the spline by moving one or more points associated with a shape of a spline.

FIG. 6 shows a GUI component 600 for editing a model of a physical system according to one embodiment of the present invention. The graphical representation of model 201 in FIG. 6 comprises information and parameters relating to the deformation characteristics of the physical model. For example, the model 201 in FIG. 6 comprises a human heart 201. Deformation information relating to a human heart may comprise information describing the change in shape of one or more chambers of the heart 201 during one or more parts of a cardiac contraction. The deformation information may further define how individual parts of the heart may move. For example, a part of the heart may comprise data indicating the part of the heart is easily deformable but very quickly returns to an undeformed state.

Figure 7:
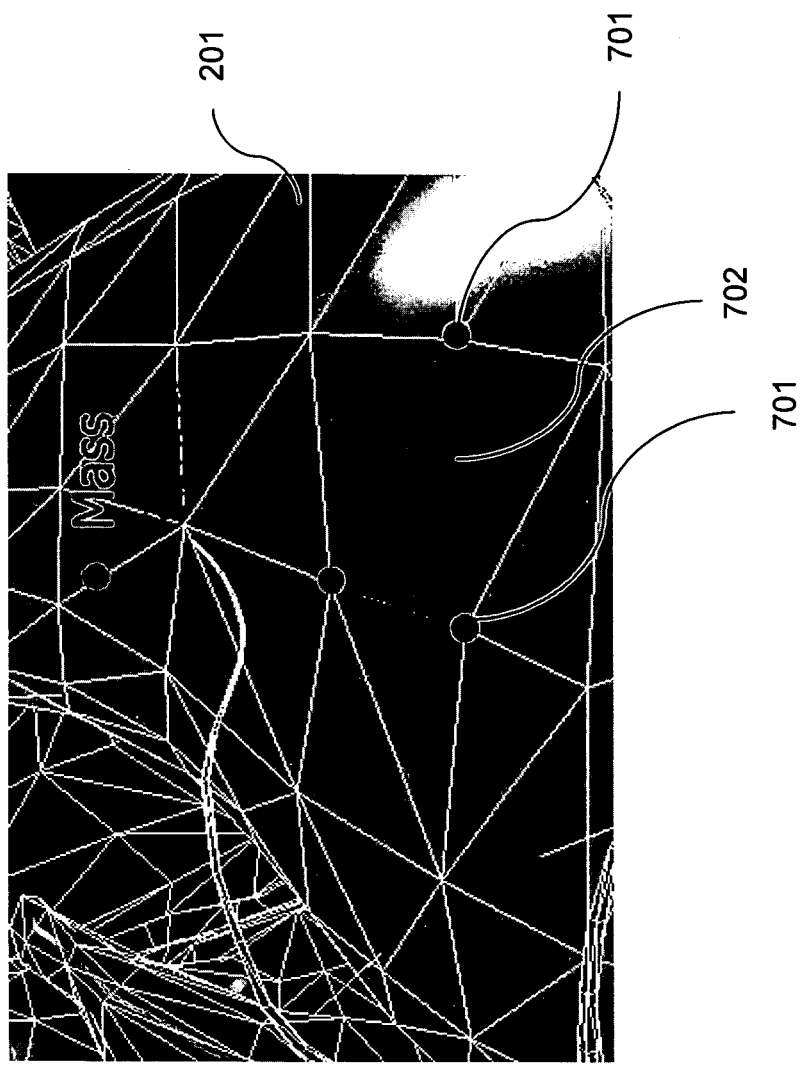
FIGS. 7 and 8 show a GUI component for editing a model of a physical system according to one embodiment of the present invention.
Figure 8:
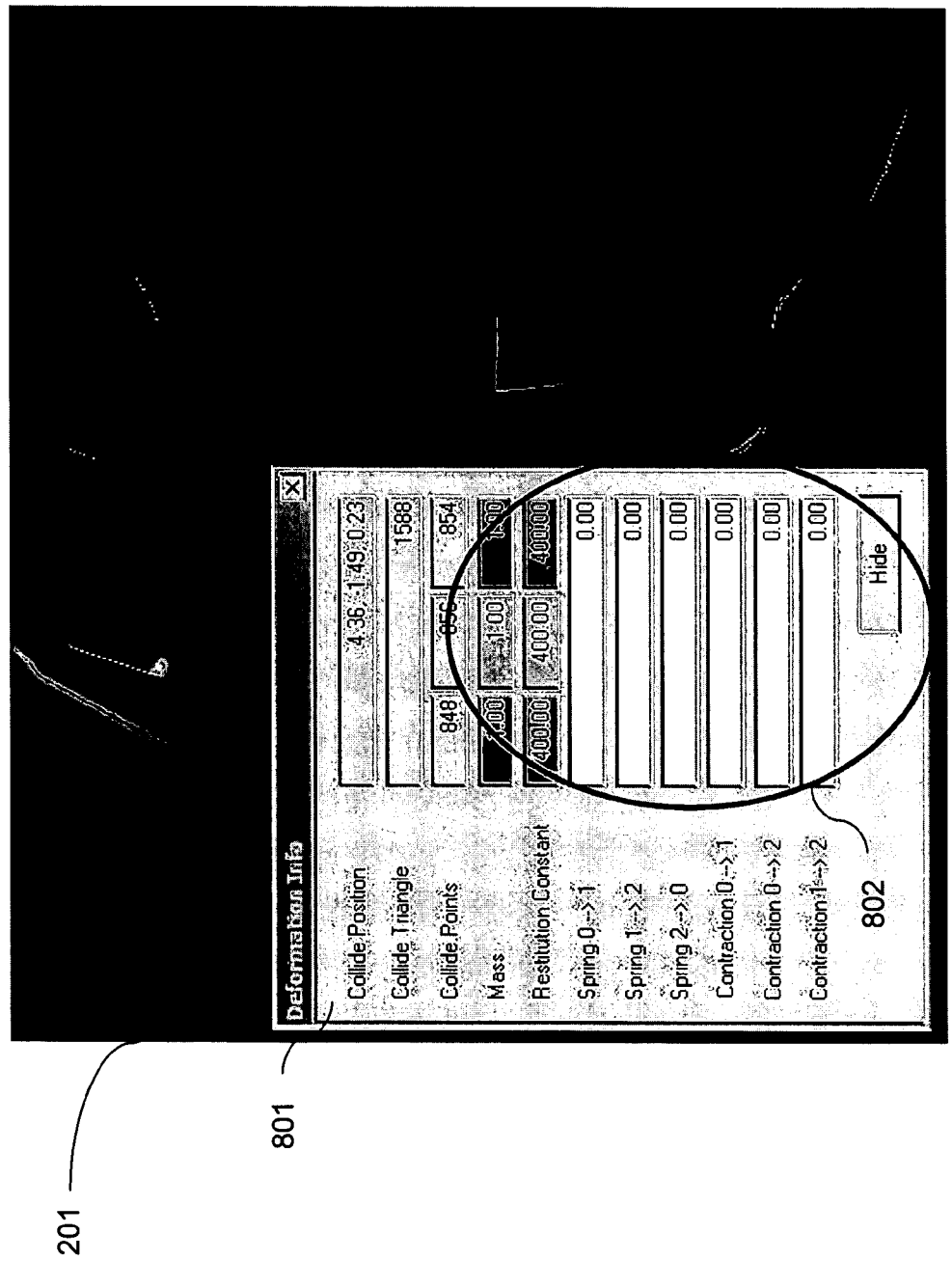

FIGS. 7 and 8 show views 700, 800 of the Deformations tab shown in FIG. 6 and a window for modifying parameters. The graphical representation visible in FIG. 7 shows a polygonal representation of the structure of the heart 201. The graphical representation further shows mass points 701 and relationships between mass points, labeled as a 'spring' 702. In one embodiment of the present invention, a mass point 701 may comprise two parameters: a mass of the mass point 701 and a restorative spring constant. In such an embodiment, the mass of the mass point 701 may indicate a resistance to movement of the mass point 701 forces applied to the mass point along one or more springs. For example, a user may employ the window 801 and parameters 802 shown in FIG. 8 to modify a mass point 701 to have a high mass value, which may cause the mass point 701 to remain substantially stationary. If a user modifies a mass point 701 to have a low mass value, the mass point 701 may move easily, or cause the system to become unstable. A restorative spring constant may provide an indication of how quickly and/or firmly a mass point 701 may return to its initial position after being moved, such as during a cardiac contraction. A user may modify the restorative spring constant to cause a mass point 701 to return to its initial position quickly, or slowly. In one embodiment, a mass may have additional associated parameters to be modified or fewer associated parameters to be modified. For example, in one embodiment, a mass point 701 may not have a user-modifiable mass and/or restorative spring constant. In one embodiment, a mass may have additional parameters, such as a maximum displacement for a mass point 701, or a different combination of parameters, which may describe a mass point 701.

In the embodiment shown in FIGS. 7 and 8, a user may further modify one or more springs 702. In the embodiment shown in FIG. 7, a spring 702 may have a spring constant and a contraction fraction. A spring constant may have a value indicating the strength of a spring 702 connecting to mass points. For example, a spring 702 modified to have a high spring constant may resist movement more strongly than a spring 702 modified to have a low spring constant.

Figure 9:
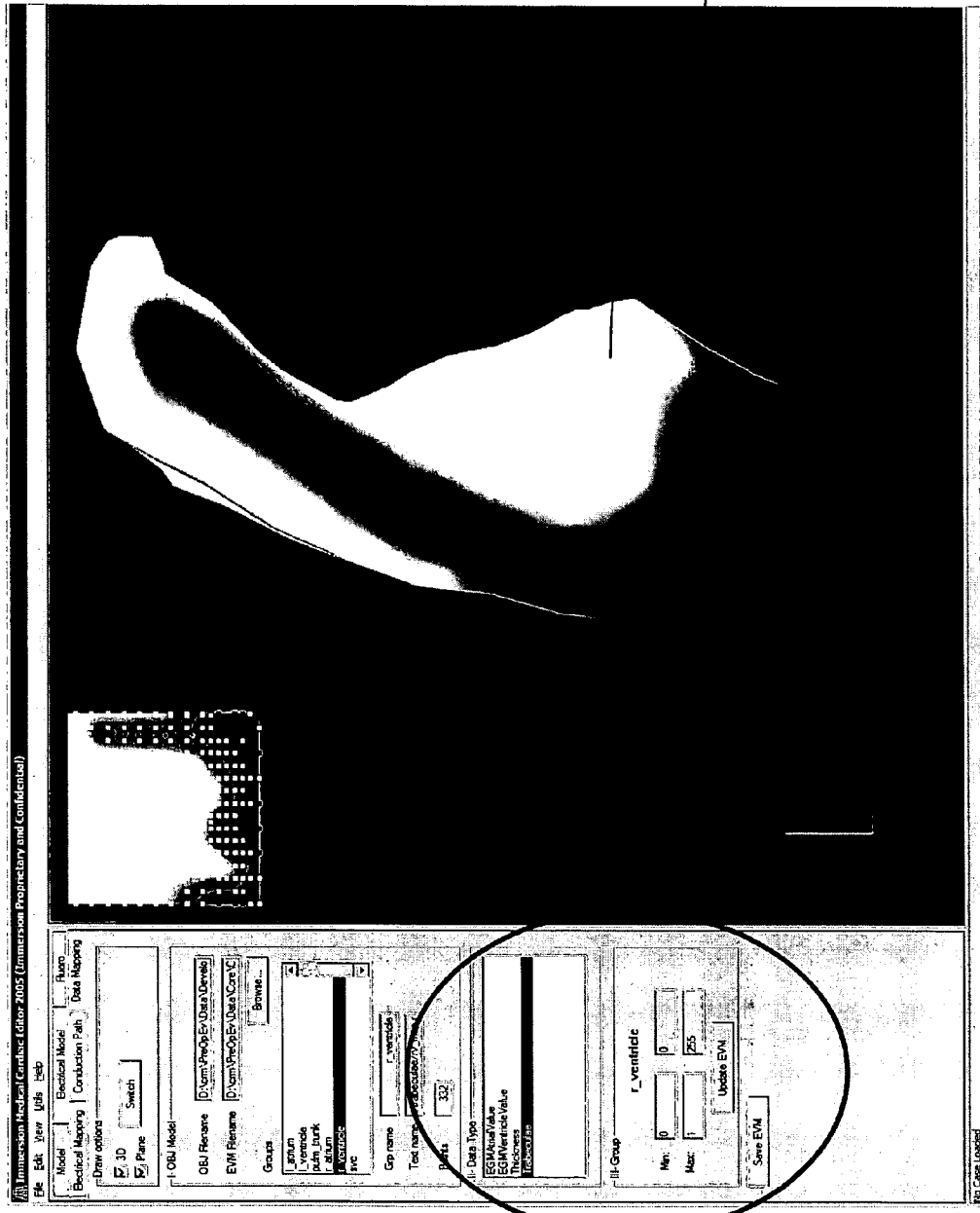
FIGS. 9 and 10 show GUI components for editing a model of a physical system according to one embodiment of the present invention.
Figure 10:
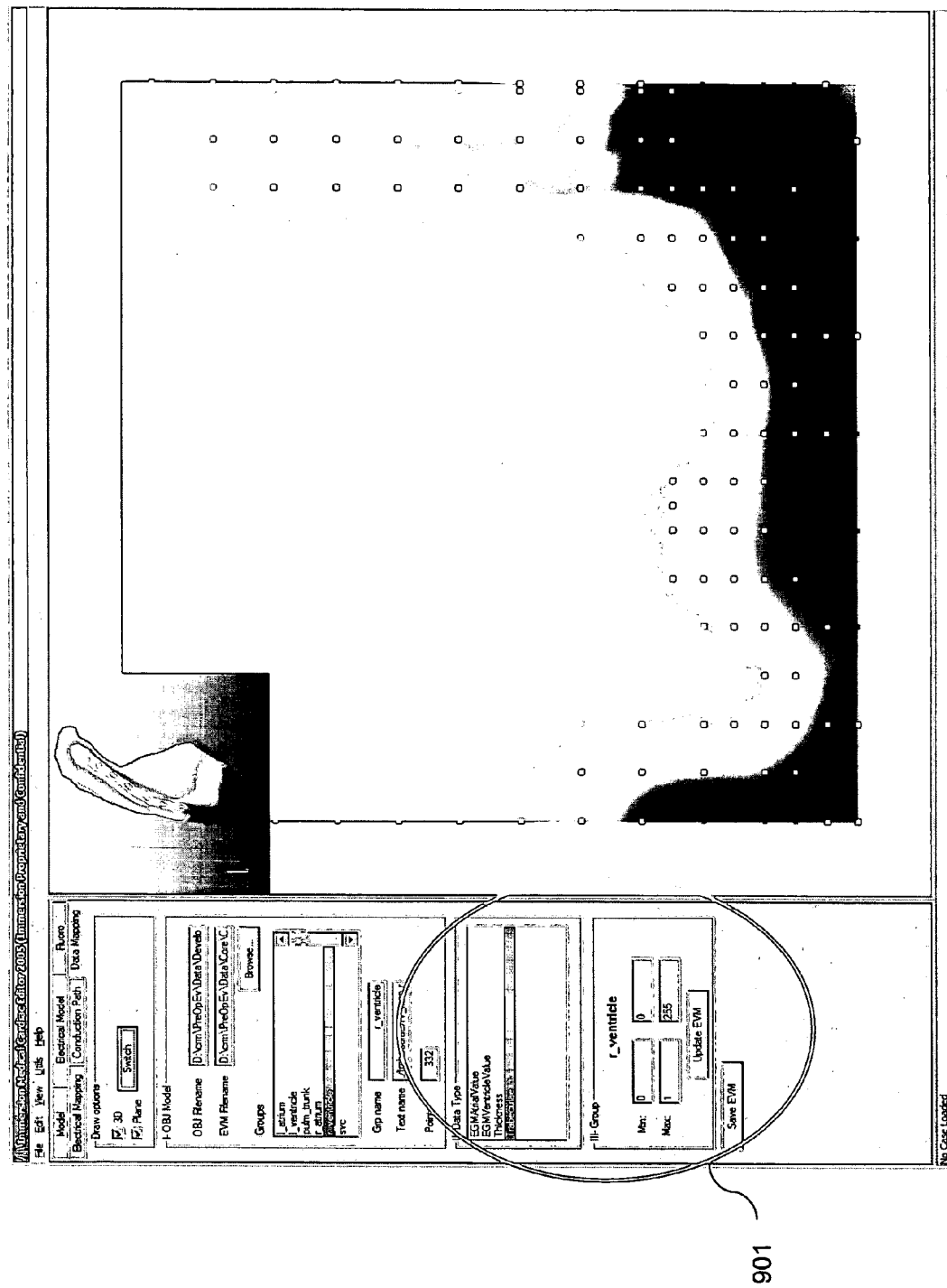

FIGS. 9 and 10 show GUI components 900, 1000 for editing a model of a physical system according to one embodiment of the present invention. The GUI components 900, 1000 shown in FIGS. 9 and 10 may allow a user to map data to a region of the model 201. For example, a user may be able to control the degree of trabeculae 901 on the surface of a particular aspect of the endocardium by mapping a value corresponding to the degree of trabeculae 901 to the geometry of the model 201. The GUI component 1000 shown in FIG. 10 shows a texture of a portion of the model 201 to which data may be mapped, while FIG. 9 shows a portion of the model 201 to which data may be mapped. Thus, the embodiment shown may provide the advantage that multiple different graphical representations of a model 201 may be provided to allow a user to more accurately modify and apply modifications to a model of a physical system.

Figure 11:
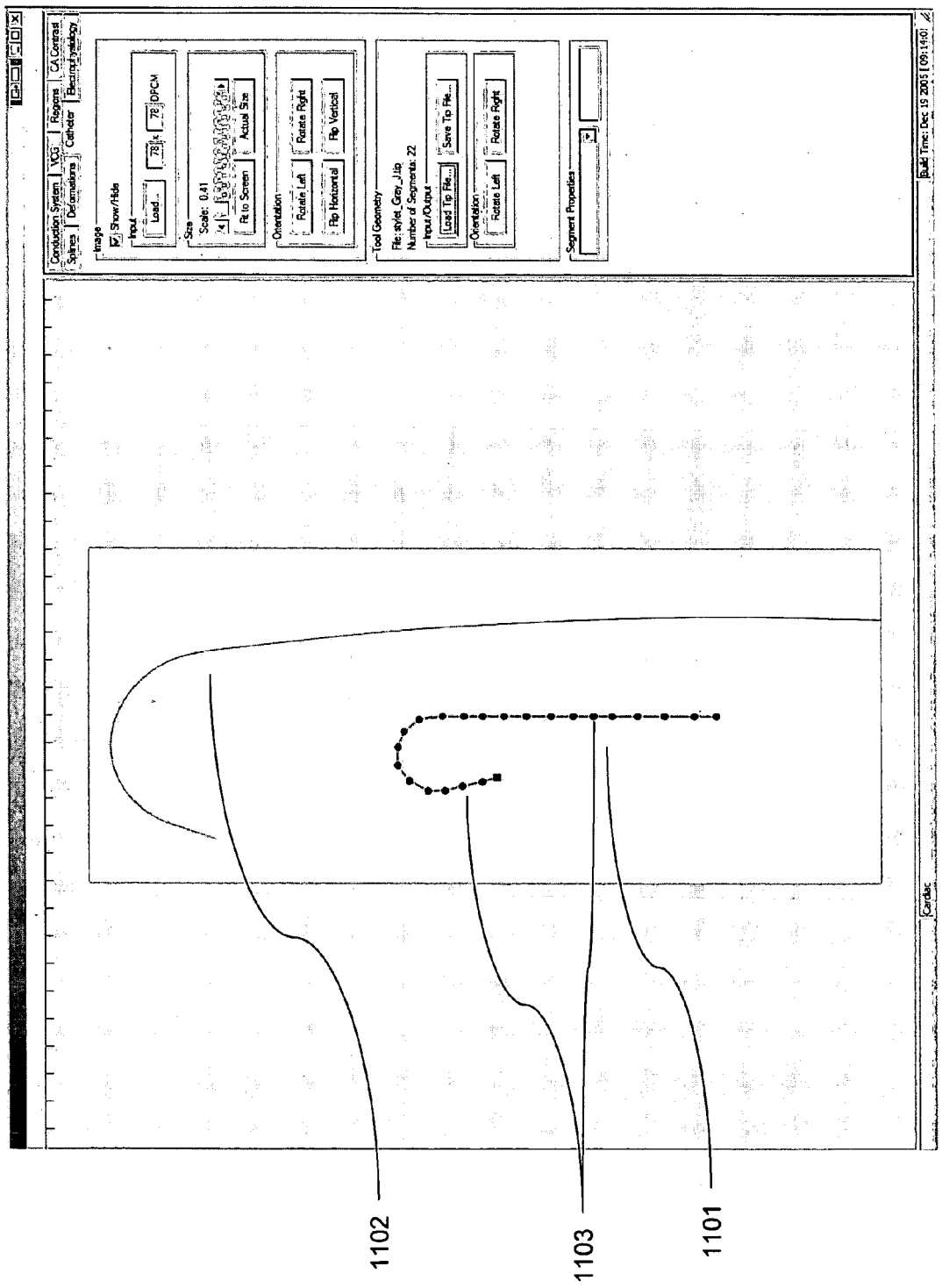
FIGS. 11 and 12 show GUI components for editing a model of a physical system according to one embodiment of the present invention.
Figure 12:
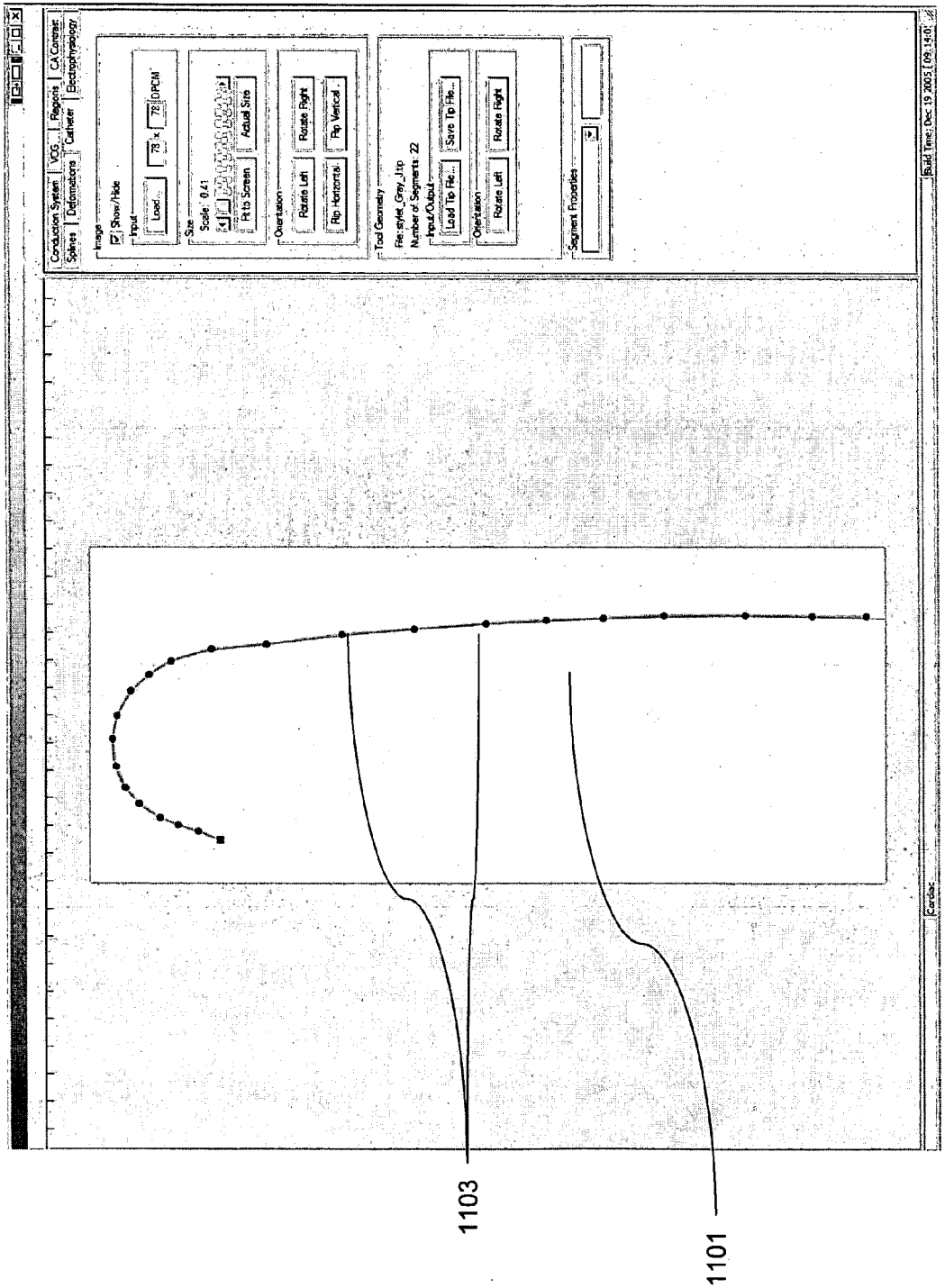

FIGS. 11 and 12 show GUI components 1100, 1200 for editing a model of a physical system according to one embodiment of the present invention. In the embodiment shown, a user may be able to modify characteristics associated with a simulated surgical device. For example, FIG. 11 shows a model 1101 of a distal tip of a catheter and a scanned image 1102 of a catheter tip. The model 1101 comprises one or more data points 1103 corresponding to one or more physical characteristics of the model 1101. A user may be able to modify a model 1101 of a tool by changing moving, modifying, deleting, or creating additional data points 1103. For example, the model 1101 of a catheter tip may be modified to more accurately represent the scanned catheter 1102, as shown in FIG. 12 by adjusting the position of the one or more data points 1103 within the model 1101. In such an embodiment, a user may be able to create or modify a model one or more tools which may be simulated.

In one embodiment of the present invention, a user may modify a model of a tool by loading a scanned image of a desired shape of the tool into memory and loading a model of a tool similar to that depicted in the scanned image, wherein the model comprises one or more points. The user may then modify one or more points to correspond with the shape of the scanned image, and store the modified model. The user may then verify the accuracy of the model by analyzing the stored model.

Figure 13:
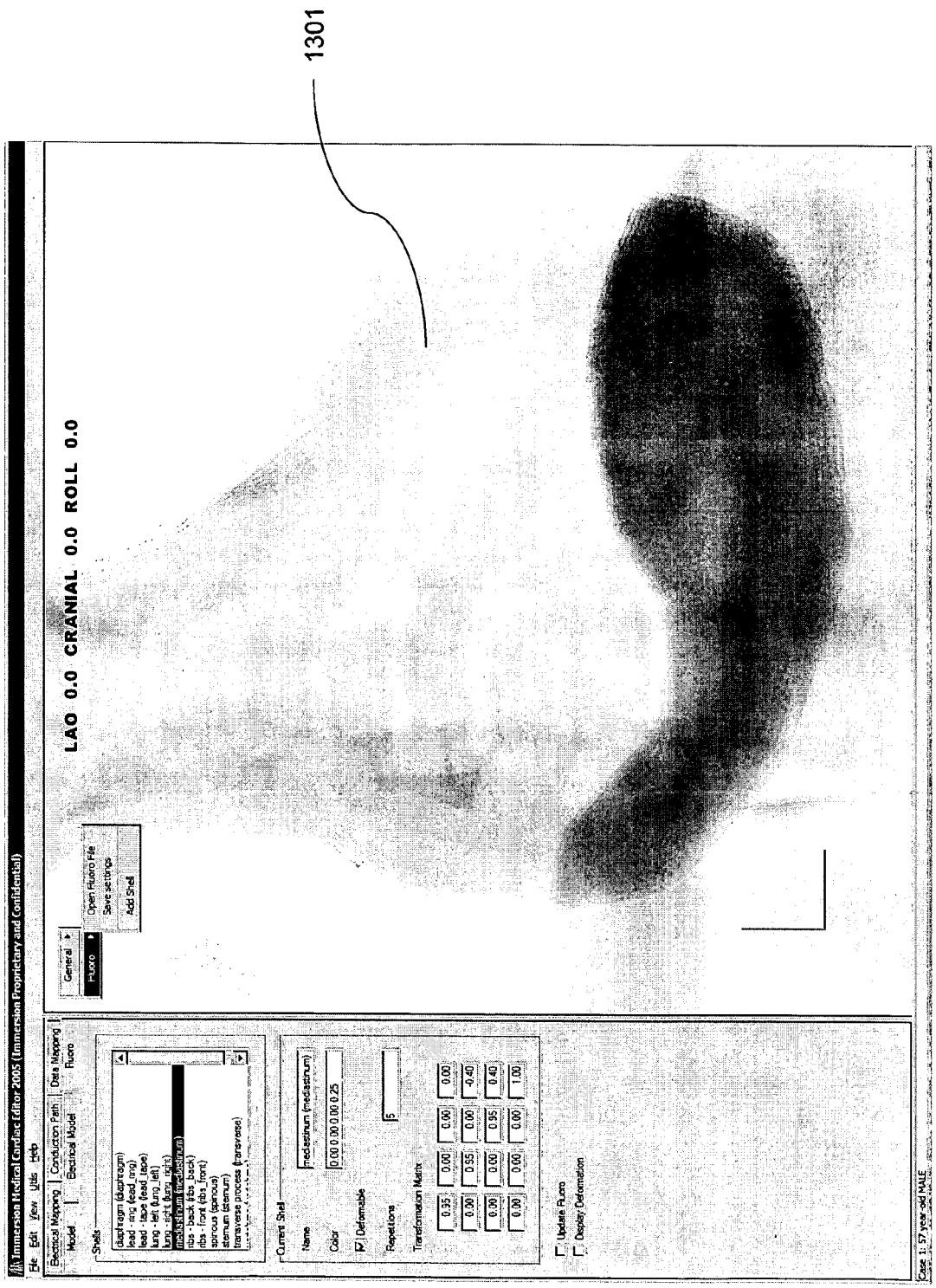
FIG. 13 shows a GUI component for editing a model of a physical system according to one embodiment of the present invention.

FIG. 13 shows a GUI component 1300 for editing a model of a physical system according to one embodiment of the present invention. The GUI component 1300 shown in FIG. 13 comprises a graphical representation of a fluoroscopic view of a model 1301 of a human heart and surrounding anatomical systems, such as a plurality of ribs, and two lungs. A user may modify one or more parameters associated with a fluoroscopic view of a model 1301, for example, by adjusting data associated with a transparency of a portion of the model 1301. For example, one or more ribs associated with the model 1301 may comprise a transparency parameter. The transparency for each rib may be separately modifiable, or all ribs may share the same transparency parameter. For example, in one embodiment of the present invention, a plurality of ribs may have a common transparency parameter for ease of editing a model. In such an embodiment, the focus of the model may be the heart, such that a fine level of control over parameters relating to the ribs may be less desirable. In one embodiment, each portion of the model may have one or more uniquely modifiable parameters. For example, a model of the heart may comprise a parameter associated with transparency; a parameter associated with a level of focus, or fuzziness; a parameter associated with color; and a parameter associated with the deformability of the portion of the model.

Figure 14:
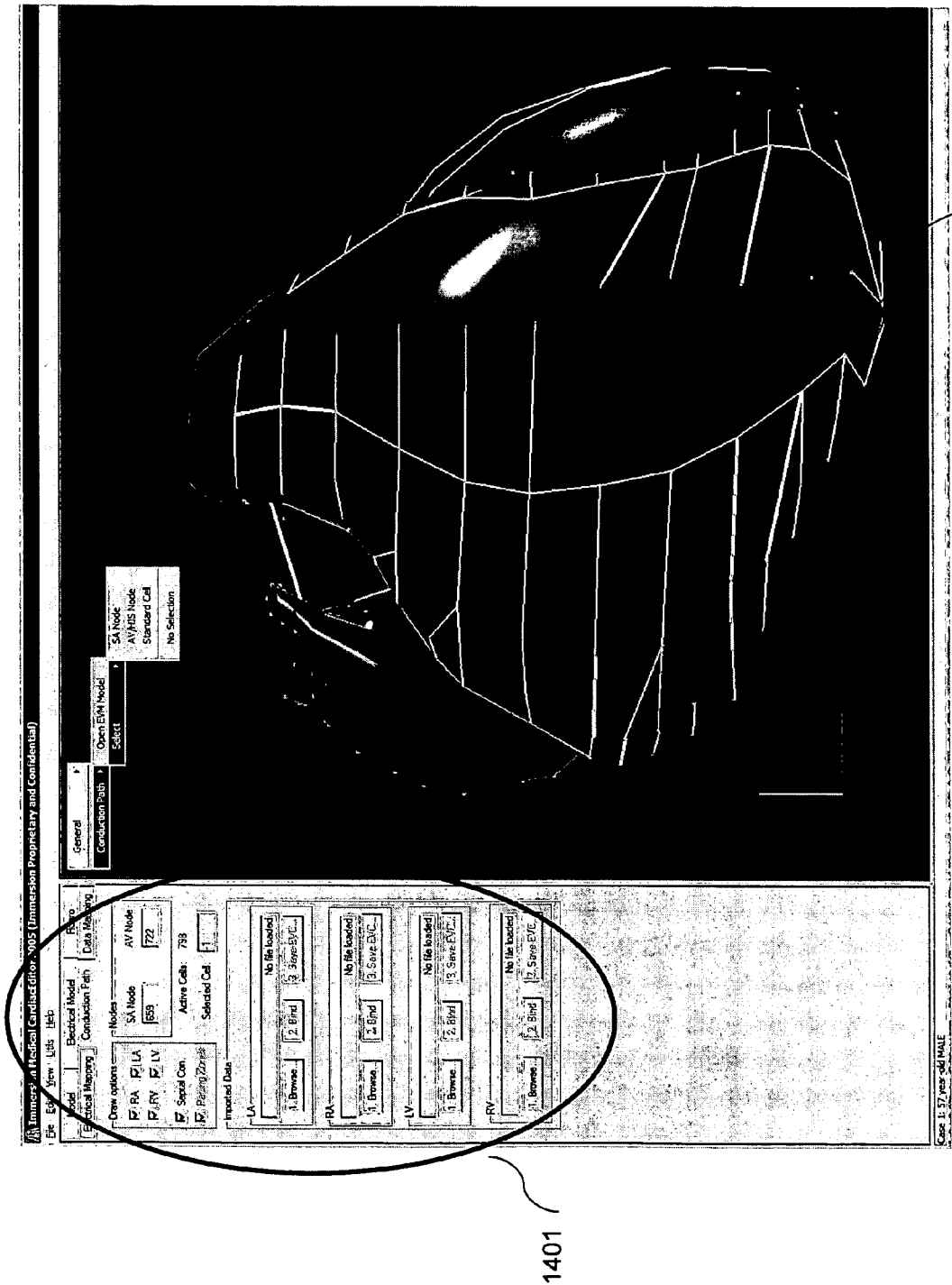
FIGS. 14 and 15 show GUI components and for editing a model of a physical system according to one embodiment of the present invention.
Figure 15:
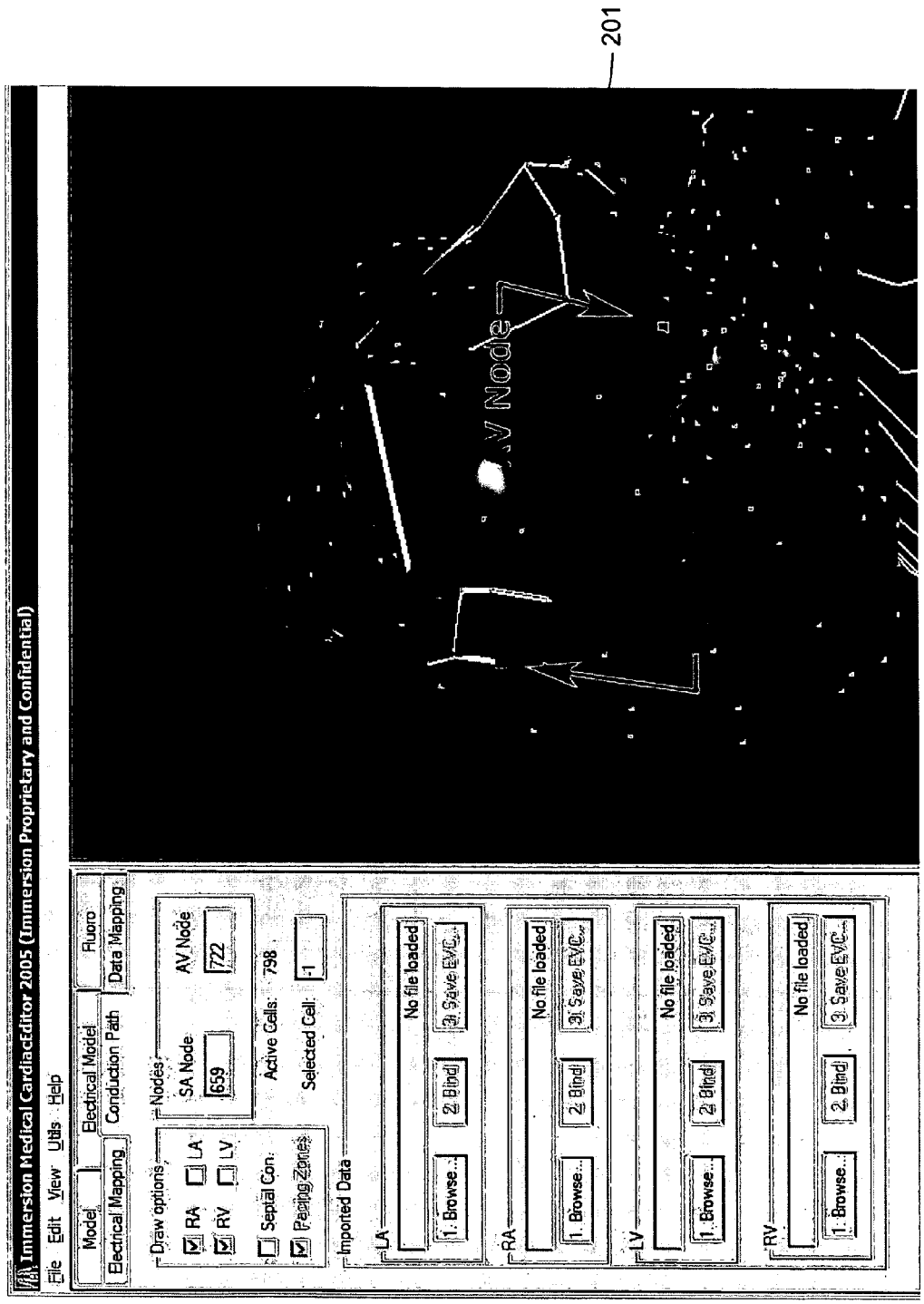

FIGS. 14 and 15 show GUI components 1400 and 1500 for editing a model of a physical system according to one embodiment of the present invention. One embodiment of the present invention may allow a mapping of information associated with a model 201 of a physical system to a point or portion of a model 201. For example, in the embodiment shown, information and/or parameters 1401 associated with the conduction paths associated with a heart may be acquired separately from data describing the structure of the heart. In one embodiment of the present invention, a user may import data associated with one or more data points defining conduction paths from a data file and map the data points to a model 201 of a human heart. For example, FIG. 15 shows a mapping of data points associated with conduction paths that have been mapped to points on a graphical representation of a model 201 of a human heart.

In one embodiment of the present invention, information relating to a physical system may be captured, for example, using an MRI, or a digitizer, or a scanner. For example, a structure of a three dimensional object, such as a car, may be digitized and stored in a computer-readable format. Information relating to systems within the car may then be captured and stored in additional data files. For example, information relating to electrical wiring may be stored in a file independently of the data associated with the three-dimensional structure of the model. In one embodiment of the present invention, the data associated with the three-dimensional structure may be loaded by an editor. In addition, data associated with the electrical wiring may be loaded by the editor as well. Using the editor, the data associated with the electrical wiring may be mapped onto the data associated with the three-dimensional structure to provide a more robust model of the physical system. The embodiment described above relates to components of a car, however, other types of physical systems may comprise multiple sources of data that may be mapped to form a more complete single model of the physical system, such as anatomical systems, mechanical systems, electrical systems, architectural plans, or other physical systems may be advantageously edited by one or more embodiments of the present invention.

Figure 16:
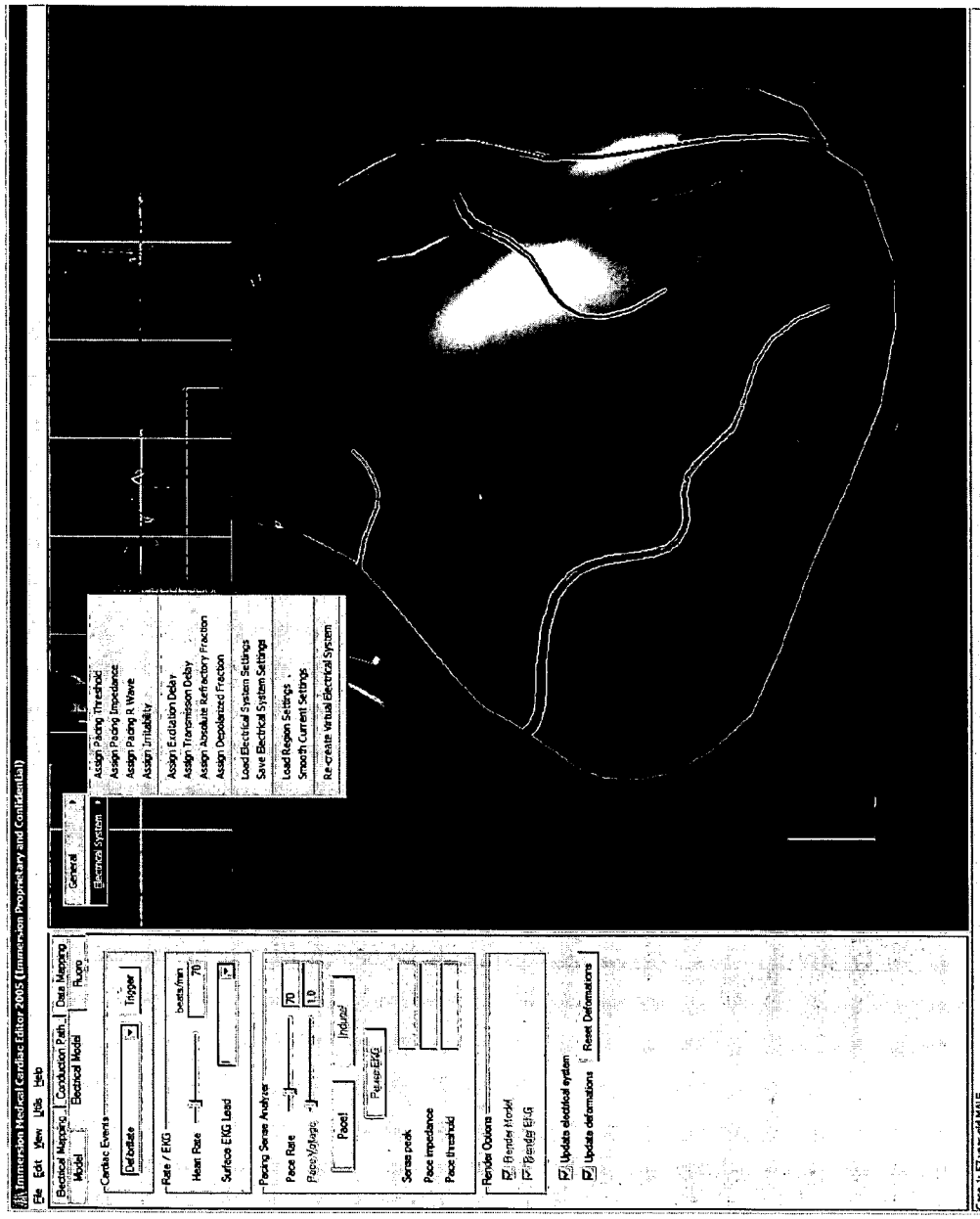
FIGS. 16-21 show GUI components of an editor according to one embodiment of the present invention.
Figure 17:
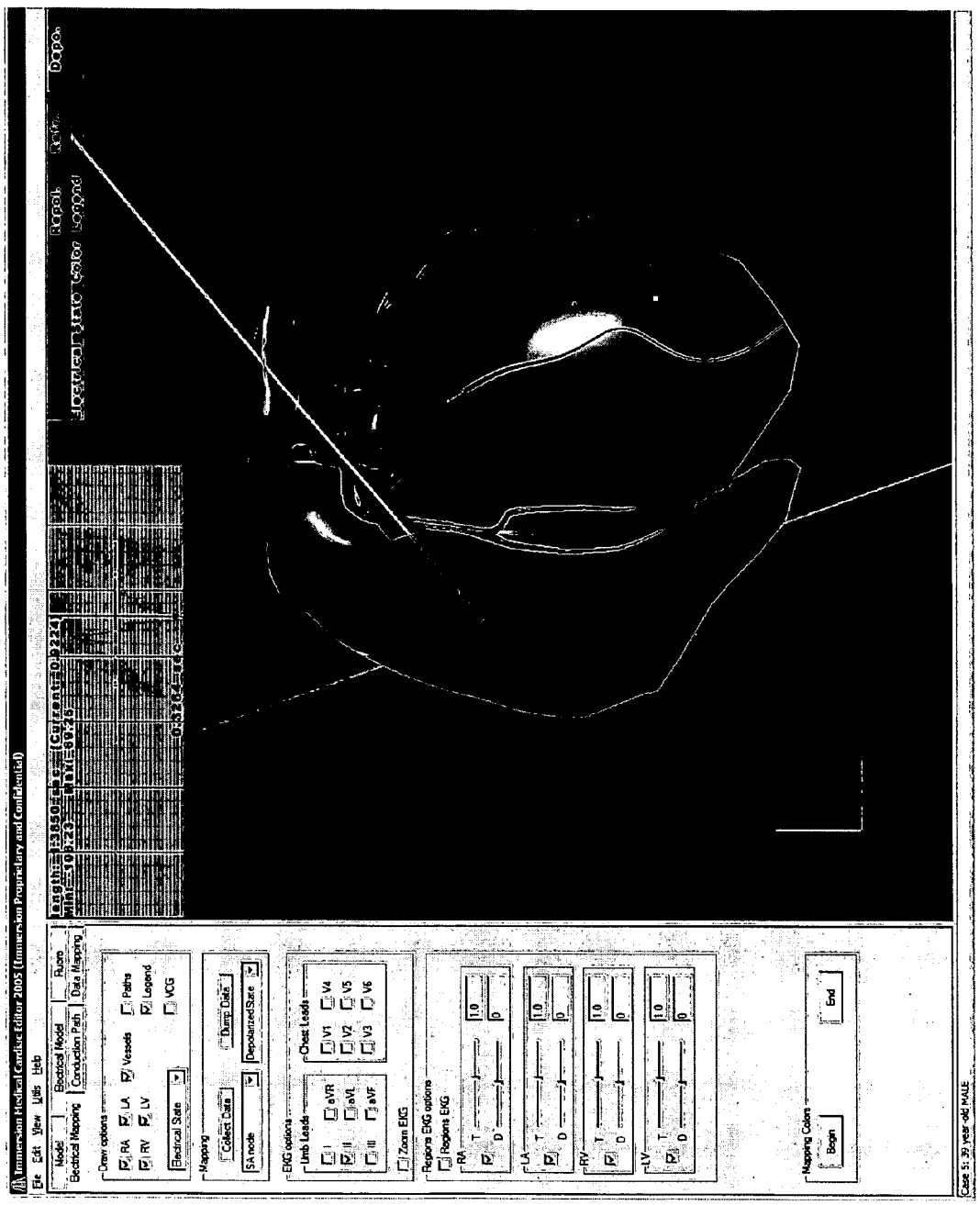
Figure 18:
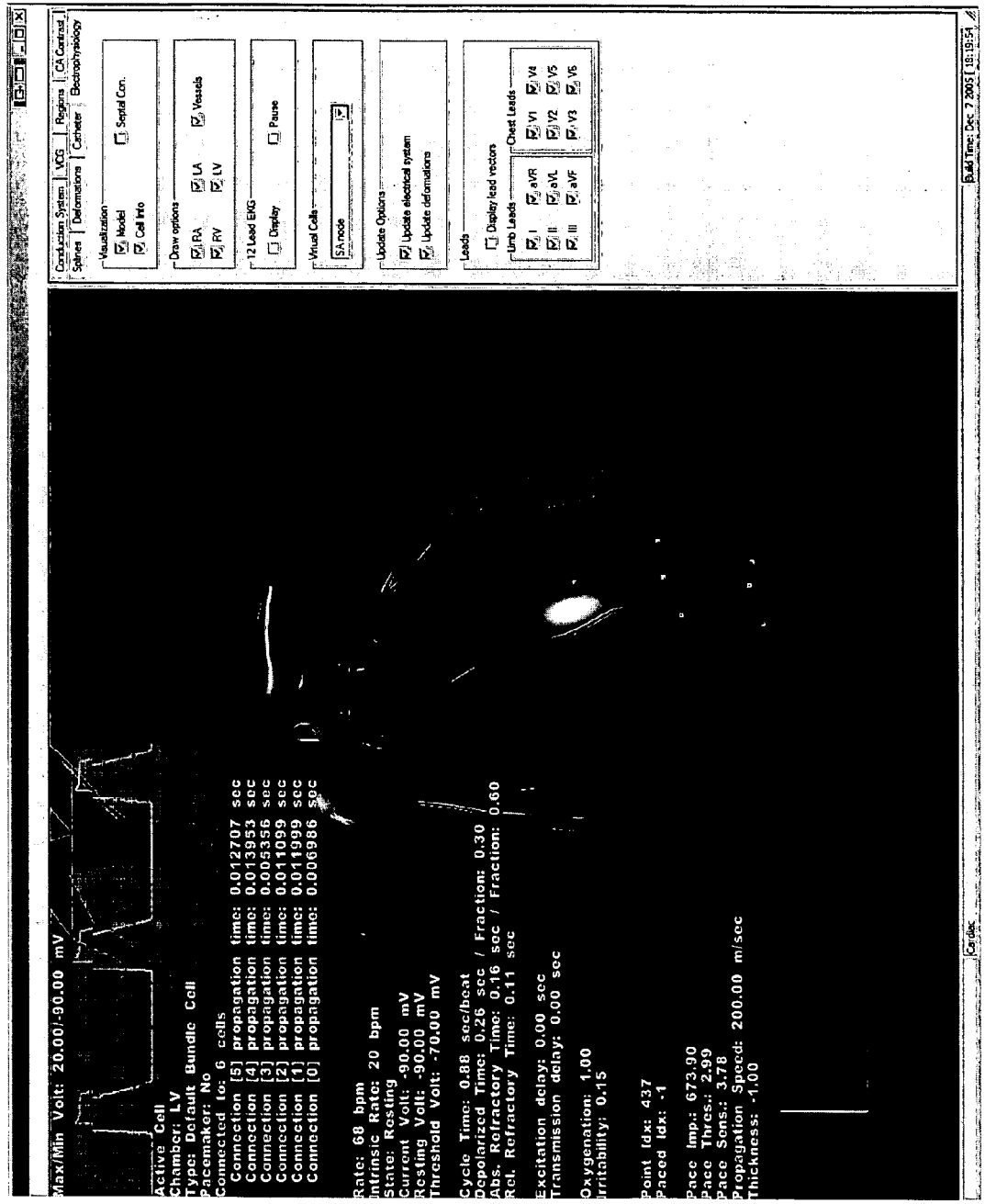
Figure 19:
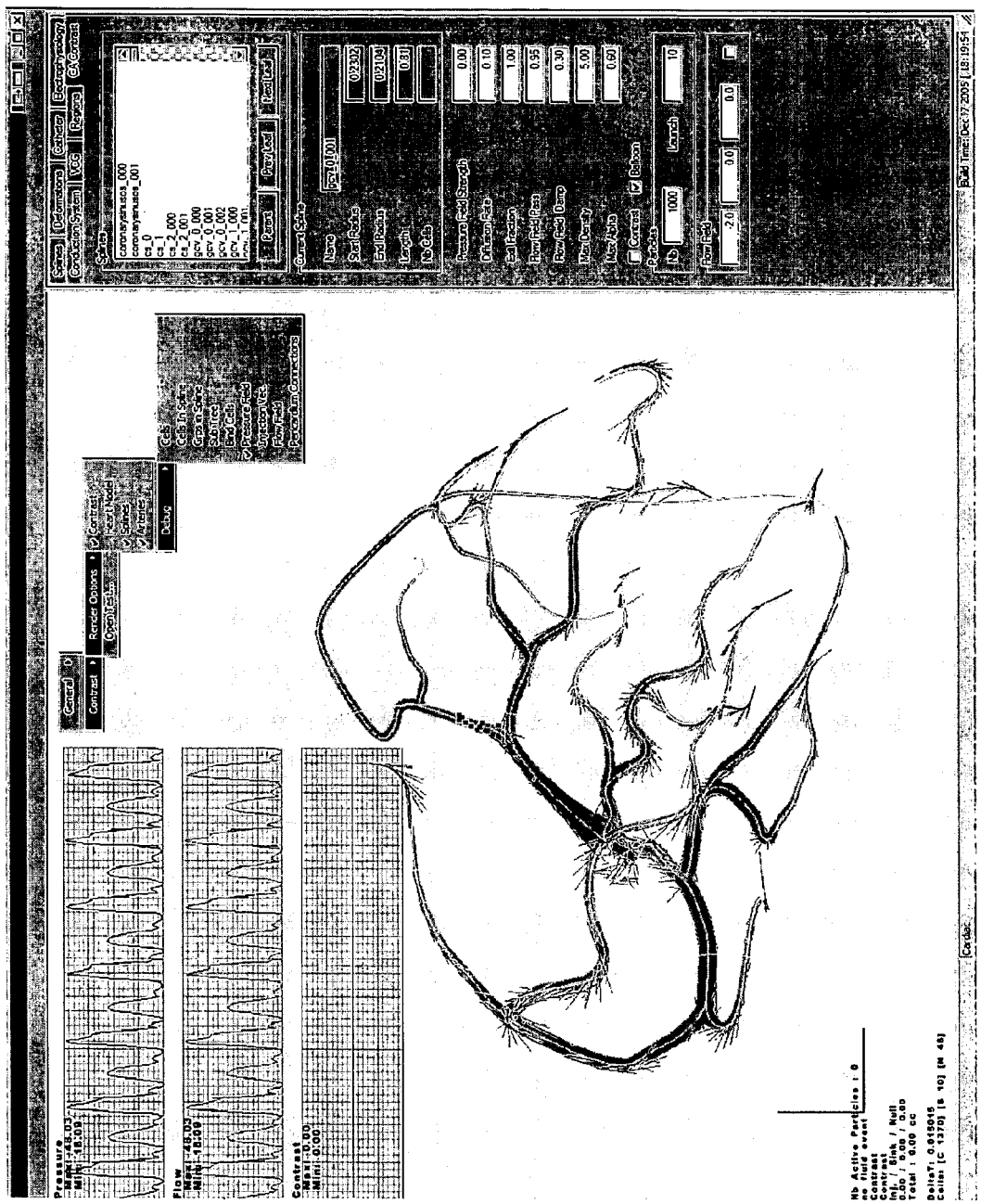
Figure 20:
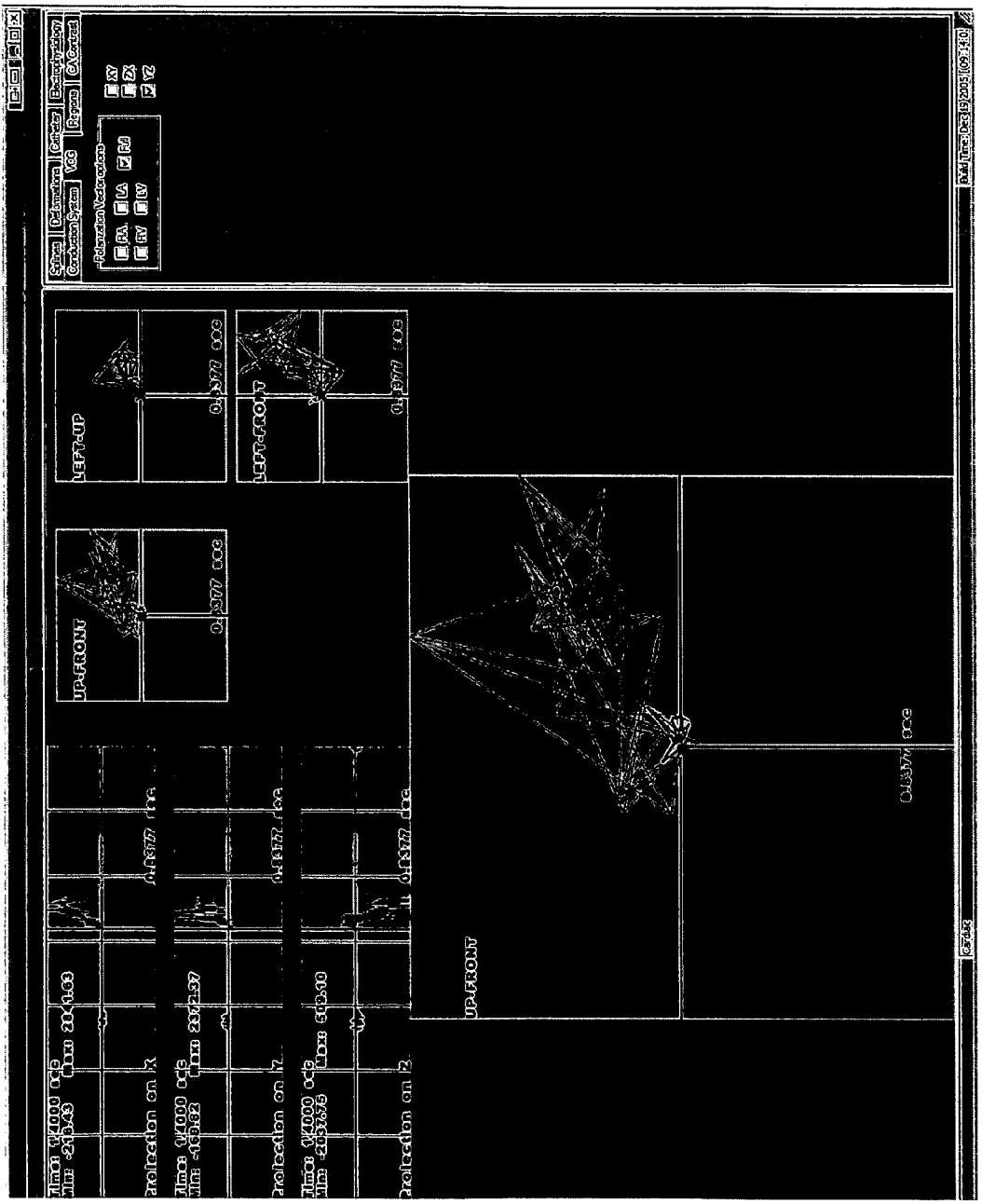
Figure 21:
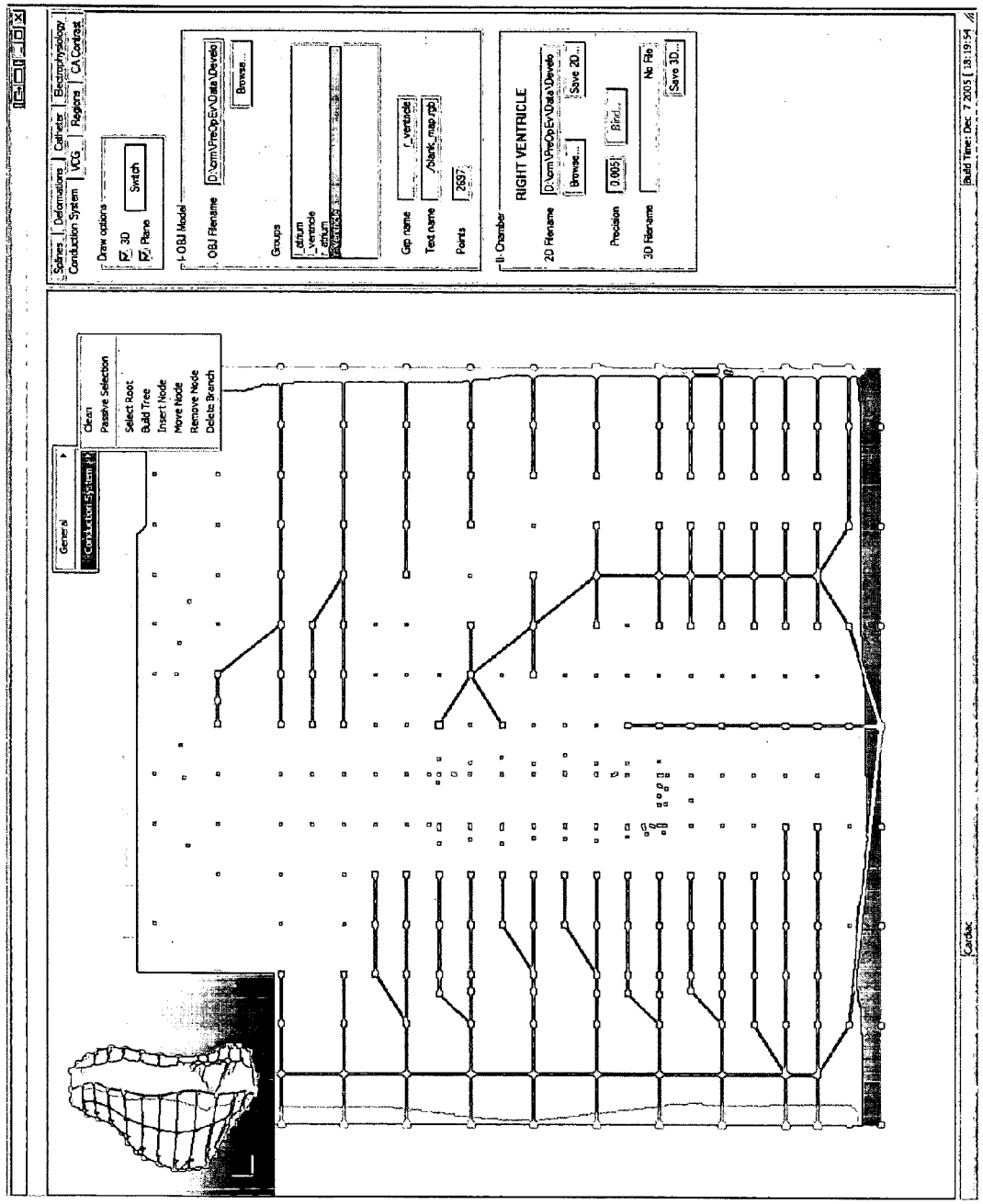

FIGS. 16-21 show GUI components of an editor according to one embodiment of the present invention. Each of FIGS. 16-21 provides a different graphical representation of a model of a physical system wherein modifications may not be allowed. For example in one embodiment, an editor may allow a visualization of the model in operation based upon the one or more parameters associated with the model. For example, FIG. 18 shows an electrophysiological representation of a model 201 of a human heart. The graphical representation in FIG. 18 may provide a graphical representation of the operation of the electrical system of a human heart 201. One embodiment of the present invention may provide a visualization of one or more systems which may allow a user to view an aspect of a model of a physical system based at least in part on parameters associated with the model. For example, FIG. 16 shows a graphical representation of the electrical system of a human heart 201, while FIG. 19 shows a graphical representation of a contrast flow system showing blood flow through a plurality of blood vessels associated with the heart 201. A user may interact with the graphical representation to view data and parameters relating to the model, however, in one embodiment, the user may not be able to modify parameters associated with the model of the human heart 201.

Illustrative Methods for Editing a Model

Figure 22:
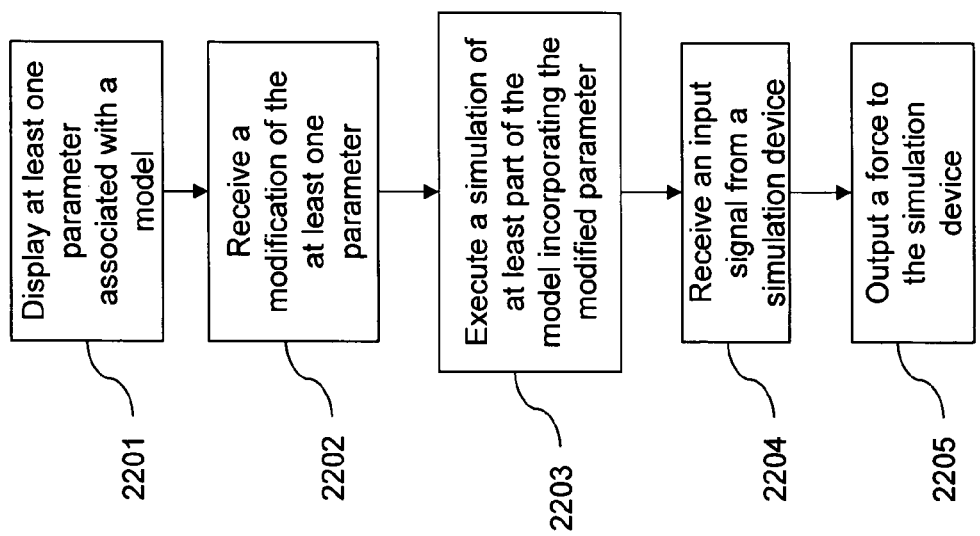
FIG. 22 shows a flowchart illustrating a method for editing a model of a physical system according to one embodiment of the present invention.

FIG. 22 shows a flowchart showing a method 2200 for editing a model of a physical system according to one embodiment of the present invention. For example, a computer 102 may execute an editor 103 and provide a GUI on a display 103 for a user to interact with while editing a model of a physical system. The method begins in block 2201 where, in one embodiment, a computer 102 displays at least one parameter associated with the model of a physical system. A computer 102 may display a parameter as text. For example, computer 102 may display a window wherein a parameter name is displayed along with a slider, text box, or other element configured to receive user input. In one embodiment, a graphical representation of a parameter may be displayed, such as a point on a model, or a highlighted section of a model.

In block 2202, a user modifies a parameter associated with a model of a physical system. The user may modify a parameter using a GUI as described according to embodiments of the invention discussed above or via other means in other embodiments. For example, a user may enter a value into a window displaying at least one parameter, wherein the value is associated with the parameter. In one embodiment, a user may interact with a graphical representation of a model, thereby modifying a parameter associated with the model. For example, a user may interact with a model and drag a portion of the model to correspond with a scanned image. The user may change a parameter associated with the model by dragging the point. In one embodiment, a user may modify a parameter associated with the model by moving a slider bar, rotating a dial, or providing input from an external device, such as a digitizer, a voltage meter, a thermocouple, or other sensor.

In block 2203, a simulation of at least the part of the model incorporating the modified parameter is executed. For example, in one embodiment, a model may comprise a human heart and one or more blood vessels providing nutrients to the heart. While editing the model of the heart, a user may modify a part of the model, such as the diameter of one of the blood vessels. An isolated simulation may then be run of the blood vessel, such that a simulation of the entire physical model is not executed. For example, the simulation may only compute interactions of the input device with the blood vessel, rather than with the entire heart. This may provide an advantage in that a user may focus on the changes made to the blood vessel without additional systems interacting with the blood vessel. For example, a user may simulate an interaction with the blood vessel without consideration for whether the movement of the input device 104 may cause a reaction in another portion of the model that may interfere with the testing of the modification to the blood vessel. Thus, the user may be able to more quickly and easily feel a haptic effect on a catheter associated with the change in blood vessel diameter without needing to execute a simulation of the entire model of the heart.

In one embodiment, a user may simulate a part of the model, wherein the part of the model is a subsystem, a subsection, a user-defined region, a component, or other mechanical or electrical characteristic of a model. In one embodiment, a user may simulate a part of the model, wherein the part comprises a time period, a single cycle of repeated action, an interaction of two components, or other temporal or spatial characteristic of the model. In one embodiment, a user may simulate an impulse response to a stimulus, a steady state response to a stimulus, a rate of change of response to a changing stimulus, or another isolated input to the model. In a further embodiment, a part of the model comprises a visual or graphical representation of the model, an audible representation of the model, or a haptic representation of the model. In a further representation, a part of the model may comprise some combination of the preceding parts of the model, or additional parts of the model not enumerated herein.

In block 2204, a user may manipulate input device 104, such as a catheter, which may cause the computer 102 to receive an input signal from the input device 104. For example, as a user manipulates the catheter, a change in position, orientation, velocity, acceleration, or other state of the catheter may change. Such a change may be transmitted to the computer 102.

In block 2205, the computer 102 may determine a force to be output on the input device 104 based at least in part on the input signal. For example, the computer 102 may receive an input signal from the input device 104 indicating a velocity. In one embodiment, the computer 102 may determine a force based on the velocity and the modified parameter. In one embodiment, the computer 102 may determine a force based on the input signal and an unmodified parameter. In one embodiment, the computer 102 may determine a force based on the input signal, an unmodified parameter, and the modified parameter. The computer may then cause the actuator 105 to output a force on the input device 104.

The foregoing description of embodiments of the invention has been presented only for the purpose of illustration and description and is not intended to be exhaustive or to limit the invention to the precise forms disclosed. Numerous modifications and adaptations thereof will be apparent to those skilled in the art without departing from the spirit and scope of the invention.

That which is claimed is:

1. A system for modifying a medical model of a physical system, comprising:
    a memory;
    a processor in communication with the memory, the processor configured to execute an editor, the editor configured to:
        receive the medical model, the medical model comprising a plurality of subsystems,
        display a graphical representation of the medical model,
        display at least one parameter associated with a first subsystem of the plurality of subsystems of the medical model,
        receive a modification of the at least one parameter, and while the medical model is within the editor:
            isolate the first subsystem, the isolating providing interaction with a graphical representation of the first subsystem during simulation of the first subsystem without the first subsystem being affected by a simulation of other subsystems, and
            execute and display a simulation of the first subsystem without executing a full simulation of the medical model in a simulated environment, the first subsystem including the modification of the at least one parameter.

2. The system of claim 1, wherein the processor is configured to store the model of the physical system including the modification of the at least one parameter.

3. The system of claim 1, further comprising an input device in communication with the processor, the input device configured to transmit an input signal to the processor, the input signal associated with a state of the input device.

4. The system of claim 3, further comprising an actuator configured to receive an actuator signal and apply a force to the input device, the force based at least in part on the input signal and the simulation.

5. The system of claim 1, wherein the physical system comprises a part of a biological organism.

6. The system of claim 5, wherein the simulation comprises an endovascular simulation.

7. The system of claim 3, wherein the input device comprises a laparoscopic device.

8. The system of claim 1, wherein the medical model comprises a model of a human heart.

9. The system of claim 1, wherein the at least one parameter comprises one or more of a size, a shape, a thickness, or a pathology.

10. A method for modifying a medical model of a physical system, comprising:
    receiving the medical model by an editor executed by a processor in communication with a memory, the medical model comprising a plurality of subsystems;
    displaying the medical model by the editor executed by a processor;
    displaying, by the editor executed by a processor, at least one parameter associated with a first subsystem of the plurality of subsystems of the medical model;
    receiving a modification of the at least one parameter by the editor executed by a processor;
    isolating the first subsystem, the isolating providing interaction with a graphical representation of the first subsystem during simulation of the first subsystem without the first subsystem being affected by a simulation of other subsystems; and
    executing and displaying, within the editor by the processor, a simulation of the first subsystem, while the medical model is within the editor, without executing a full simulation of the medical model in a simulated environment, the first subsystem including the modification of the at least one parameter.

11. The method of claim 10, further comprising receiving an input signal associated with a state of an input device.

12. The method of claim 11, further comprising outputting a force to the input device, the force based at least in part on the input signal and the simulation of the at least part of the medical model including the modification of the at least one parameter.

13. The method of claim 10, storing the medical model including the modification of the at least one parameter.

14. The method of claim 10, wherein the physical system comprises a part of a biological organism.

15. The method of claim 14, wherein the simulation comprises an endovascular simulation.

16. The method of claim 11, wherein the input device comprises a laparoscopic device.

17. The method of claim 10, wherein the medical model comprises a model of the human heart.

18. The method of claim 10, wherein the at least one parameter comprises one or more of a size, a shape, a thickness, or a pathology.

19. A non-transitory computer-readable medium comprising program code for modifying a medical model of a physical system, comprising:
    program code for receiving the medical model by an editor executed by a processor in communication with a memory, the medical model comprising a plurality of subsystems;
    program code for displaying the medical model by the editor executed by a processor
    program code for displaying, by the editor executed by a processor, at least one parameter associated with a first subsystem of the model of the physical system;
    program code for receiving a modification of the at least one parameter by the editor executed by a processor;
    program code for isolating the first subsystem, the isolating providing interaction with a graphical representation of the first subsystem during simulation of the first subsystem without the first subsystem being affected by a simulation of other subsystems; and
    program code for executing and displaying, within the editor by the processor, a simulation of the first subsystem, while the medical model is within the editor, without executing a full simulation of the medical model in a simulated environment, the first subsystem including the modification of the at least one parameter.

20. The non-transitory computer-readable medium of claim 19, further comprising program code for receiving an input signal associated with the state of an input device.

21. The non-transitory computer-readable medium of claim 20, further comprising program code for outputting a force to the input device, the force based at least in part on the input signal and the simulation of the part of medical the model of the physical system including the modification of the at least one parameter.

22. The non-transitory computer-readable medium of claim 19, further comprising program code for storing the medical model of the physical system including the modification of the at least one parameter.

23. The non-transitory computer-readable medium of claim 19, wherein the physical system comprises a part of a biological organism.

24. The non-transitory computer-readable medium of claim 23, wherein the simulation comprises an endovascular simulation.

25. The non-transitory computer-readable medium of claim 19, wherein the input device comprises a laparoscopic device.

26. The non-transitory computer-readable medium of claim 19, wherein the medical model comprises a model of the human heart.

27. The non-transitory computer-readable medium of claim 19, wherein the at least one parameter comprises one or more of a size, a shape, a thickness, or a pathology.

* * * * *

UNITED STATES PATENT AND TRADEMARK OFFICE
CERTIFICATE OF CORRECTION

| | | |
|---|---|---|
| PATENT NO. | : 8,639,485 B2 | Page 1 of 1 |
| APPLICATION NO. | : 11/599521 | |
| DATED | : January 28, 2014 | |
| INVENTOR(S) | : Hugh Connacher et al. | |

It is certified that error appears in the above-identified patent and that said Letters Patent is hereby corrected as shown below:

In the Claims:

Column 16, Line 48, should read - subsystem of the plurality of subsystems of the model of the physical system;

Signed and Sealed this
Fifteenth Day of April, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,639,485 B2 | Page 1 of 1 |
| APPLICATION NO. | : 11/599521 | |
| DATED | : January 28, 2014 | |
| INVENTOR(S) | : Connacher et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 839 days.

Signed and Sealed this
Eleventh Day of August, 2015

Michelle K. Lee
*Director of the United States Patent and Trademark Office*